US011497507B2

(12) United States Patent
Culbert et al.

(10) Patent No.: US 11,497,507 B2
(45) Date of Patent: Nov. 15, 2022

(54) SYSTEMS AND METHODS FOR CLOSING PORTIONS OF BODY TISSUE

(71) Applicant: ORPHEUS VENTURES, LLC, Irvine, CA (US)

(72) Inventors: Bradley S. Culbert, Mission Viejo, CA (US); Bartosz Bojanowski, San Francisco, CA (US); Eric Rowson, Laguna Niguel, CA (US)

(73) Assignee: Orpheus Ventures, LLC, Irvine, CA (US)

( * ) Notice: Subject to any disclaimer, the term of this patent is extended or adjusted under 35 U.S.C. 154(b) by 135 days.

(21) Appl. No.: 15/898,616

(22) Filed: Feb. 18, 2018

(65) Prior Publication Data

US 2018/0235636 A1 Aug. 23, 2018

Related U.S. Application Data

(60) Provisional application No. 62/460,837, filed on Feb. 19, 2017.

(51) Int. Cl.
*A61B 17/128* (2006.01)
*A61B 5/00* (2006.01)
(Continued)

(52) U.S. Cl.
CPC ............ *A61B 17/128* (2013.01); *A61B 5/489* (2013.01); *A61B 5/6847* (2013.01); *A61B 8/12* (2013.01);
(Continued)

(58) Field of Classification Search
CPC . A61B 17/128; A61B 17/10; A61B 17/12009; A61B 17/1227; A61B 17/1285;
(Continued)

(56) References Cited

U.S. PATENT DOCUMENTS 3,856,017 A 12/1974 Perisse et al.
4,090,517 A 5/1978 Takenaka
(Continued)

FOREIGN PATENT DOCUMENTS

CN 1628622 A 6/2005
CN 2865738 Y 7/2007
(Continued)

OTHER PUBLICATIONS

PCT International Search Report and Written Opinion for PCT/US2018/018586, Applicant: Orpheus Ventures, LLC, Forms PCT/ISA/220, 210, and 237 dated May 25, 2018 (13 pages).
(Continued)

*Primary Examiner* — Brooke Nicole Labranche
(74) *Attorney, Agent, or Firm* — Blair Walker IP Services, LLC

(57) ABSTRACT

A system for closing a blood vessel includes a housing having a proximal end and a distal end and configured to be held in the hand of a user, an elongate body extending from the distal end of the housing, a distal housing having a proximal end coupled to a distal end of the elongate body and having a cavity including an opening on a side of the distal housing, a lumen passing through the elongate body and terminating at the cavity of the distal housing and configured to couple to a vacuum source, a sensor carried by the distal housing adjacent the cavity and configured for identifying a blood vessel, wherein the lumen is configured to maintain a vacuum within the cavity when a probe having a vessel closure module is inserted within the lumen and the vessel closure module is within the cavity.

20 Claims, 10 Drawing Sheets

(51) Int. Cl.
*A61B 17/12* (2006.01)
*A61B 17/10* (2006.01)
*A61B 17/122* (2006.01)
*A61B 8/12* (2006.01)
*A61B 18/14* (2006.01)
*A61B 8/08* (2006.01)
*A61B 8/00* (2006.01)
*A61B 18/00* (2006.01)
*A61B 90/00* (2016.01)
*A61B 17/00* (2006.01)
*A61B 17/30* (2006.01)

(52) U.S. Cl.
CPC ........ *A61B 17/10* (2013.01); *A61B 17/12009* (2013.01); *A61B 17/1227* (2013.01); *A61B 17/1285* (2013.01); *A61B 18/1485* (2013.01); *A61B 8/4444* (2013.01); *A61B 8/488* (2013.01); *A61B 17/12013* (2013.01); *A61B 2017/00057* (2013.01); *A61B 2017/00106* (2013.01); *A61B 2017/00407* (2013.01); *A61B 2017/00818* (2013.01); *A61B 2017/308* (2013.01); *A61B 2018/005* (2013.01); *A61B 2018/00291* (2013.01); *A61B 2018/00863* (2013.01); *A61B 2018/144* (2013.01); *A61B 2018/1407* (2013.01); *A61B 2090/062* (2016.02); *A61B 2505/05* (2013.01)

(58) Field of Classification Search
CPC . A61B 17/12013; A61B 5/489; A61B 5/6847; A61B 8/12; A61B 8/4444; A61B 8/488; A61B 18/1485; A61B 2090/062; A61B 2017/00057; A61B 2017/00106; A61B 2017/00407; A61B 2017/00818; A61B 2017/308; A61B 2018/00291; A61B 2018/005; A61B 2018/00863; A61B 2018/1407; A61B 2018/144; A61B 2505/05
See application file for complete search history.

(56) References Cited

U.S. PATENT DOCUMENTS

| | | |
|---|---|---|
| 4,142,529 A | 3/1979 | Latenser et al. |
| 4,227,535 A | 10/1980 | Conner |
| 4,257,419 A | 3/1981 | Goltner et al. |
| 4,493,319 A | 1/1985 | Polk et al. |
| 4,513,746 A | 4/1985 | Aranyi et al. |
| 4,548,201 A | 10/1985 | Yoon |
| 4,566,620 A | 1/1986 | Green et al. |
| 4,621,635 A | 11/1986 | Ali |
| 4,638,806 A | 1/1987 | Bartlett |
| 4,696,302 A | 9/1987 | Clark et al. |
| 4,735,194 A | 4/1988 | Stiegmann |
| 4,794,927 A | 1/1989 | Yoon |
| 4,834,067 A | 5/1989 | Block |
| 4,860,746 A | 8/1989 | Yoon |
| 4,898,169 A | 2/1990 | Norman et al. |
| D308,723 S | 6/1990 | Bellofatto et al. |
| 4,932,397 A | 6/1990 | McFaul, Sr. |
| 4,936,842 A | 6/1990 | D'Amelio et al. |
| 5,122,149 A | 6/1992 | Broome |
| 5,156,315 A | 10/1992 | Green et al. |
| 5,158,563 A | 10/1992 | Cosman |
| 5,178,627 A | 1/1993 | Hudock |
| 5,192,266 A | 3/1993 | Wilk |
| 5,203,863 A | 4/1993 | Bidoia |
| 5,263,926 A | 11/1993 | Wilk |
| 5,269,789 A | 12/1993 | Chin et al. |
| 5,312,361 A | 5/1994 | Zadini et al. |
| 5,320,630 A | 6/1994 | Ahmed |
| 5,356,416 A | 10/1994 | Chu et al. |
| 5,395,030 A | 3/1995 | Kuramoto et al. |
| 5,423,834 A | 6/1995 | Ahmed |
| 5,437,664 A | 8/1995 | Cohen et al. |
| 5,462,559 A | 10/1995 | Ahmed |
| 5,464,412 A | 11/1995 | Budding |
| 5,570,692 A | 11/1996 | Morinaga |
| 5,578,047 A | 11/1996 | Taylor |
| 5,624,453 A | 4/1997 | Ahmed |
| 5,651,788 A | 7/1997 | Fleischer et al. |
| 5,676,637 A | 10/1997 | Lee |
| 5,690,692 A | 11/1997 | Fleming |
| 5,741,273 A | 4/1998 | O'Regan |
| 5,746,694 A | 5/1998 | Wilk et al. |
| 5,788,715 A | 8/1998 | Watson, Jr. et al. |
| 5,830,222 A | 11/1998 | Makower |
| 5,853,416 A | 12/1998 | Tolkoff |
| 5,879,347 A | 3/1999 | Saadat |
| 5,891,134 A | 4/1999 | Goble et al. |
| 5,913,865 A | 6/1999 | Fortier et al. |
| 5,921,983 A | 7/1999 | Shannon, Jr. |
| 5,924,423 A | 7/1999 | Majlessi |
| 5,976,158 A | 11/1999 | Adams et al. |
| 5,980,537 A | 11/1999 | Ouchi |
| 6,007,551 A | 12/1999 | Peifer et al. |
| 6,024,742 A | 2/2000 | Tu et al. |
| RE36,629 E | 3/2000 | Zaslavsky et al. |
| 6,033,397 A | 3/2000 | Laufer et al. |
| 6,042,591 A | 3/2000 | Mears |
| 6,050,993 A | 4/2000 | Tu et al. |
| 6,051,003 A | 4/2000 | Chu et al. |
| 6,059,797 A | 5/2000 | Mears |
| 6,066,145 A | 5/2000 | Wurster |
| 6,077,257 A | 6/2000 | Edwards et al. |
| 6,135,997 A | 10/2000 | Laufer et al. |
| 6,136,009 A | 10/2000 | Mears |
| 6,139,527 A | 10/2000 | Laufer et al. |
| 6,142,933 A | 11/2000 | Longo et al. |
| 6,152,899 A | 11/2000 | Farley et al. |
| 6,179,832 B1 | 1/2001 | Jones et al. |
| 6,206,842 B1 | 3/2001 | Tu et al. |
| 6,206,843 B1 | 3/2001 | Iger et al. |
| 6,235,040 B1 | 5/2001 | Chu et al. |
| 6,258,087 B1 | 7/2001 | Edwards et al. |
| 6,263,248 B1 | 7/2001 | Farley et al. |
| 6,273,886 B1 | 8/2001 | Edwards et al. |
| 6,315,782 B1 | 11/2001 | Chu et al. |
| 6,325,798 B1 | 12/2001 | Edwards et al. |
| 6,346,105 B1 | 2/2002 | Tu et al. |
| 6,355,031 B1 | 3/2002 | Edwards et al. |
| 6,358,248 B1 | 3/2002 | Mulier et al. |
| 6,401,719 B1 | 6/2002 | Farley et al. |
| 6,405,732 B1 | 6/2002 | Edwards et al. |
| 6,409,737 B1 | 6/2002 | Fortier et al. |
| 6,419,673 B1 | 7/2002 | Edwards et al. |
| 6,419,683 B1 | 7/2002 | Burgard |
| 6,423,058 B1 | 7/2002 | Edwards et al. |
| 6,436,108 B1 | 8/2002 | Mears |
| 6,464,708 B1 | 10/2002 | Higuma et al. |
| 6,482,184 B1 | 11/2002 | Christensen et al. |
| 6,506,157 B1 | 1/2003 | Teigman et al. |
| 6,547,798 B1 | 4/2003 | Yoon et al. |
| 6,626,922 B1 | 9/2003 | Hart et al. |
| 6,632,233 B1 | 10/2003 | Burgard |
| 6,645,201 B1 | 11/2003 | Utley et al. |
| 6,682,526 B1 | 1/2004 | Jones et al. |
| 6,685,713 B1 | 2/2004 | Ahmed |
| 6,688,312 B2 | 2/2004 | Yeretsian |
| 6,695,764 B2 | 2/2004 | Silverman et al. |
| 6,699,243 B2 | 3/2004 | West et al. |
| 6,706,057 B1 | 3/2004 | Bidoia et al. |
| 6,730,101 B1 | 5/2004 | Peifer et al. |
| 6,743,197 B1 | 6/2004 | Edwards |
| 6,827,715 B2 | 12/2004 | Francischelli et al. |
| 6,923,756 B2 | 8/2005 | Sudakov et al. |
| 6,936,005 B2 | 8/2005 | Poff et al. |
| 6,936,055 B1 | 8/2005 | Ken et al. |
| 6,969,388 B2 | 11/2005 | Goldman et al. |
| 6,974,466 B2 | 12/2005 | Ahmed et al. |
| 7,037,314 B2 | 5/2006 | Armstrong |

(56) References Cited

U.S. PATENT DOCUMENTS

| | | |
|---|---|---|
| 7,097,644 B2 | 8/2006 | Long |
| 7,118,528 B1 | 10/2006 | Piskun |
| 7,137,981 B2 | 11/2006 | Long |
| 7,160,294 B2 | 1/2007 | Croft |
| 7,179,257 B2 | 2/2007 | West et al. |
| 7,189,247 B1 | 3/2007 | Zirps et al. |
| 7,214,231 B2 | 5/2007 | Tolkoff |
| 7,270,670 B1 | 9/2007 | Yencho |
| 7,364,579 B2 | 4/2008 | Mulier et al. |
| 7,422,587 B2 | 9/2008 | Bek et al. |
| 7,452,329 B2 | 11/2008 | Bastia et al. |
| 7,488,333 B2 | 2/2009 | Ghareeb |
| 7,507,238 B2 | 3/2009 | Edwards et al. |
| 7,608,073 B2 | 10/2009 | Heinrich et al. |
| 7,641,652 B2 | 1/2010 | Coe et al. |
| 7,695,432 B2 | 4/2010 | Scheyer |
| 7,717,312 B2 | 5/2010 | Beetel |
| 7,722,627 B2 | 5/2010 | Andreen |
| 7,789,848 B2 | 9/2010 | Gannoe et al. |
| 7,789,876 B2 | 9/2010 | Zikorus et al. |
| 7,794,460 B2 | 9/2010 | Mulier et al. |
| 7,824,408 B2 | 11/2010 | Mirizzi et al. |
| 7,846,149 B2 | 12/2010 | Jankowski |
| 7,896,895 B2 | 3/2011 | Boudreaux et al. |
| 7,905,891 B2 | 3/2011 | Self |
| 7,972,354 B2 | 7/2011 | Prestezog et al. |
| 7,977,658 B2 | 7/2011 | Stuba et al. |
| 3,066,009 A1 | 11/2011 | Blurton et al. |
| 8,083,738 B2 | 12/2011 | Mirizzi et al. |
| 8,097,002 B2 | 1/2012 | Delaney |
| 8,097,003 B2 | 1/2012 | Hoffman et al. |
| 8,100,822 B2 | 1/2012 | Piskun |
| 8,131,380 B2 | 3/2012 | Cao et al. |
| 8,211,101 B2 | 7/2012 | Croft |
| 8,287,535 B2 | 10/2012 | de la Mora Levy et al. |
| 8,290,582 B2 | 10/2012 | Lin et al. |
| 8,292,904 B2 | 10/2012 | Popovic et al. |
| 8,303,605 B2 | 11/2012 | Bastia |
| 8,328,060 B2 | 12/2012 | Jankowski et al. |
| 8,343,026 B2 | 1/2013 | Gardiner et al. |
| 8,357,157 B2 | 1/2013 | Mirizzi et al. |
| 8,394,012 B2 | 3/2013 | Szinicz |
| 8,412,318 B2 | 4/2013 | Edwards et al. |
| 8,430,808 B2 | 4/2013 | Piskun |
| 8,491,607 B1 | 7/2013 | Horppuu et al. |
| 8,496,578 B2 | 7/2013 | Surti |
| 8,506,477 B2 | 8/2013 | Waller et al. |
| 8,545,433 B2 | 10/2013 | Brandeis |
| 8,579,892 B2 | 11/2013 | Hoey et al. |
| 8,591,525 B2 | 11/2013 | Ikeda |
| 8,632,458 B2 | 1/2014 | Piskun et al. |
| 8,647,352 B2 | 2/2014 | Noda et al. |
| 8,672,829 B2 | 3/2014 | Kaleta et al. |
| 8,678,264 B2 | 3/2014 | Racenet et al. |
| 8,684,248 B2 | 4/2014 | Milliman |
| 8,686,040 B2 | 4/2014 | Ehrenpreis |
| 8,696,660 B2 | 4/2014 | West et al. |
| 8,715,166 B2 | 5/2014 | Piskun |
| 8,715,276 B2 | 5/2014 | Thompson et al. |
| 8,728,074 B2 | 5/2014 | West et al. |
| 8,734,826 B2 | 5/2014 | Barak |
| 8,747,300 B2 | 6/2014 | Frassica et al. |
| 8,758,340 B2 | 6/2014 | Ford et al. |
| 8,790,686 B2 | 7/2014 | Carroll |
| 8,801,650 B2 | 8/2014 | Gannoe et al. |
| 8,932,306 B1 | 1/2015 | McGown |
| 8,968,275 B2 | 3/2015 | Piskun et al. |
| 8,968,353 B2 | 3/2015 | Prestezog et al. |
| 9,011,317 B2 | 4/2015 | Piskun et al. |
| 9,011,486 B2 | 4/2015 | Raabe et al. |
| 9,017,361 B2 | 4/2015 | Karabey et al. |
| 9,039,601 B2 | 5/2015 | Piskun |
| 9,078,736 B2 | 7/2015 | Matsuo |
| 9,179,966 B2 | 11/2015 | Newton et al. |
| 9,192,291 B2 | 11/2015 | Wenchell |
| 9,232,947 B2 | 1/2016 | Brenner et al. |
| 9,310,956 B2 | 4/2016 | Shikhman et al. |
| 9,393,014 B2 | 7/2016 | Milliman |
| 2002/0013581 A1 | 1/2002 | Edwards et al. |
| 2002/0062130 A1 | 5/2002 | Jugenheimer et al. |
| 2002/0072738 A1 | 6/2002 | Edwards et al. |
| 2002/0072757 A1 | 6/2002 | Ahmed et al. |
| 2002/0072761 A1 | 6/2002 | Abrams et al. |
| 2002/0107515 A1 | 8/2002 | Edwards et al. |
| 2002/0147447 A1 | 10/2002 | Long |
| 2002/0177847 A1 | 11/2002 | Long |
| 2003/0069592 A1 | 4/2003 | Adams et al. |
| 2003/0144653 A1 | 7/2003 | Francischelli et al. |
| 2003/0144715 A1 | 7/2003 | Gomez |
| 2003/0181900 A1 | 9/2003 | Long |
| 2003/0229359 A1 | 12/2003 | Fortier |
| 2004/0010216 A1 | 1/2004 | Zhu et al. |
| 2004/0138527 A1 | 7/2004 | Bonner et al. |
| 2005/0143756 A1 | 6/2005 | Jankowski |
| 2005/0187546 A1 | 8/2005 | Bek et al. |
| 2005/0277945 A1 | 12/2005 | Saadat et al. |
| 2006/0004384 A1 | 1/2006 | Andreen |
| 2006/0020231 A1 | 1/2006 | Naraikin et al. |
| 2006/0025766 A1 | 2/2006 | Heinrich et al. |
| 2006/0030849 A1 | 2/2006 | Mirizzi et al. |
| 2006/0036190 A1 | 2/2006 | Naraikin et al. |
| 2006/0036191 A1 | 2/2006 | Naraykin et al. |
| 2006/0036192 A1 | 2/2006 | Naraikin et al. |
| 2006/0036193 A1 | 2/2006 | Naraikin et al. |
| 2006/0049231 A1 | 3/2006 | Leiboff et al. |
| 2006/0064124 A1 | 3/2006 | Zhu et al. |
| 2006/0089660 A1 | 4/2006 | Saeed et al. |
| 2006/0167473 A1 | 7/2006 | Scheyer |
| 2006/0189979 A1 | 8/2006 | Esch et al. |
| 2006/0259041 A1 | 11/2006 | Hoffman et al. |
| 2006/0259042 A1 | 11/2006 | Ali Hassanien |
| 2006/0264706 A1 | 11/2006 | Piskun |
| 2007/0213661 A1 | 9/2007 | Gobel |
| 2007/0213747 A1 | 9/2007 | Monassevitch et al. |
| 2007/0225734 A1 | 9/2007 | Bell et al. |
| 2007/0260163 A1 | 11/2007 | Blurton et al. |
| 2008/0058786 A1 | 3/2008 | Boyden et al. |
| 2008/0188875 A1 | 8/2008 | Yeretsian |
| 2008/0281204 A1 | 11/2008 | Salfi et al. |
| 2008/0281267 A1 | 11/2008 | Meheir |
| 2009/0069806 A1 | 3/2009 | De La Mora Levy et al. |
| 2009/0105728 A1 | 4/2009 | Noda et al. |
| 2009/0143794 A1* | 6/2009 | Conlon ............ A61B 18/1482 606/167 |
| 2009/0149846 A1 | 6/2009 | Hoey et al. |
| 2010/0099944 A1 | 4/2010 | Shalon et al. |
| 2010/0130857 A1 | 5/2010 | Szinicz |
| 2010/0152529 A1 | 6/2010 | Shalon et al. |
| 2010/0262133 A1 | 10/2010 | Hoey et al. |
| 2010/0331862 A1 | 12/2010 | Monassevitch et al. |
| 2011/0083264 A1 | 4/2011 | Gunderson |
| 2011/0092766 A1 | 4/2011 | Monassevitch et al. |
| 2011/0137428 A1 | 6/2011 | Terliuc |
| 2011/0160748 A1 | 6/2011 | Catanese, III et al. |
| 2011/0282344 A1* | 11/2011 | Whayne ............ A61B 18/082 606/49 |
| 2012/0004546 A1 | 1/2012 | Neuberger et al. |
| 2012/0059394 A1 | 3/2012 | Brenner et al. |
| 2012/0130403 A1 | 5/2012 | Brenner et al. |
| 2012/0226334 A1 | 9/2012 | Gardiner et al. |
| 2014/0107483 A1 | 4/2014 | Utley et al. |
| 2014/0264081 A1* | 9/2014 | Walker ............ G01B 11/14 250/459.1 |
| 2015/0126990 A1 | 5/2015 | Sharma et al. |
| 2016/0074039 A1 | 3/2016 | Beetel |
| 2016/0338719 A1* | 11/2016 | Allen, IV ............ A61B 90/03 |
| 2016/0375274 A1* | 12/2016 | Barthe ............ A61B 8/5223 601/3 |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |

(56) References Cited

U.S. PATENT DOCUMENTS

2019/0125458 A1  5/2019  Shelton, IV et al.
2019/0125459 A1  5/2019  Shelton, IV et al.

FOREIGN PATENT DOCUMENTS

| CN | 201029911 Y | 3/2008 |
|---|---|---|
| CN | 103126654 A | 6/2013 |
| CN | 104856649 A | 8/2015 |
| DE | 9205453 U1 | 6/1992 |
| EP | 0136949 A2 | 4/1985 |
| JP | 2506390 B2 | 6/1996 |
| JP | 2510074 B2 | 6/1996 |
| JP | 2004105678 A | 4/2004 |
| JP | 3902290 B2 | 4/2007 |
| JP | 4171177 B2 | 10/2008 |
| WO | WO0003642 | 1/2000 |
| WO | WO2001091646 A1 | 12/2001 |
| WO | WO2004064624 A1 | 8/2004 |
| WO | WO2007019321 A2 | 2/2007 |
| WO | WO2007093198 A1 | 8/2007 |
| WO | WO2008081436 A2 | 7/2008 |
| WO | WO2016/118041 A1 | 7/2016 |

OTHER PUBLICATIONS

Machine translation (English) CN 103126654 A (21 pages).
Machine translation (English) CN 104856649 A (14 pages).
Extended European Search Report dated Dec. 11, 2019, in EP App. No. 18754988.6 filed Feb. 19, 2018 (7 pages).

\* cited by examiner

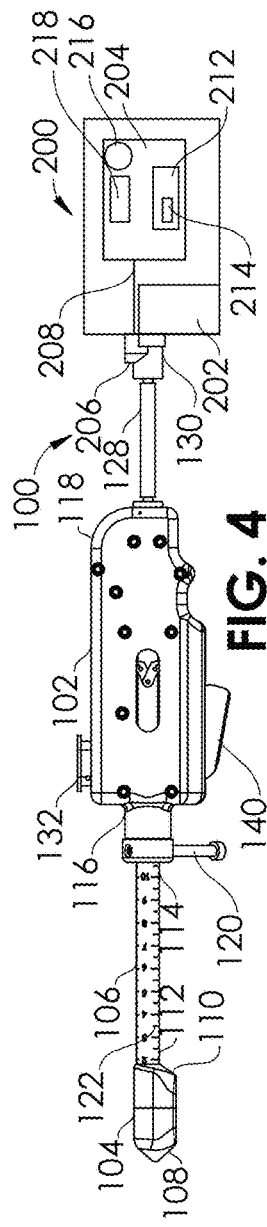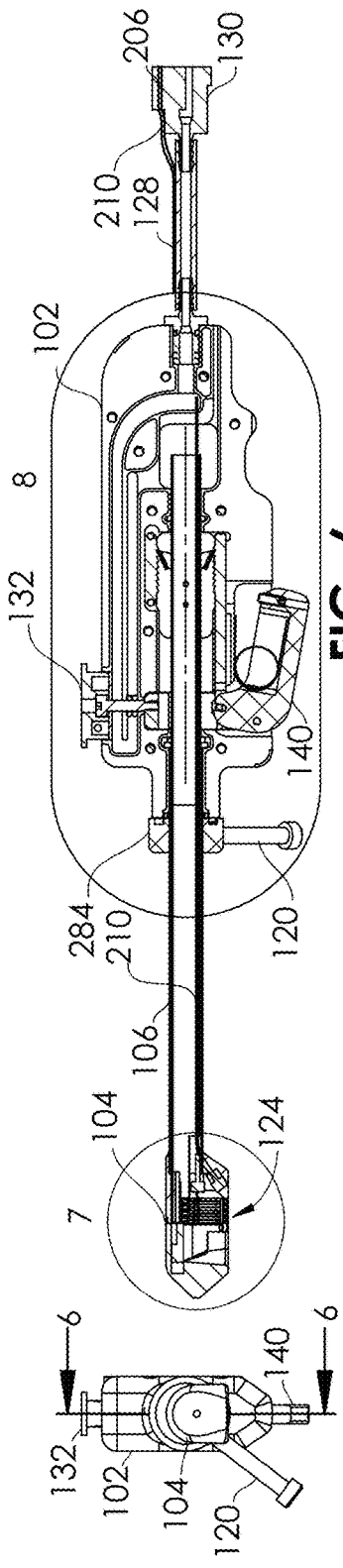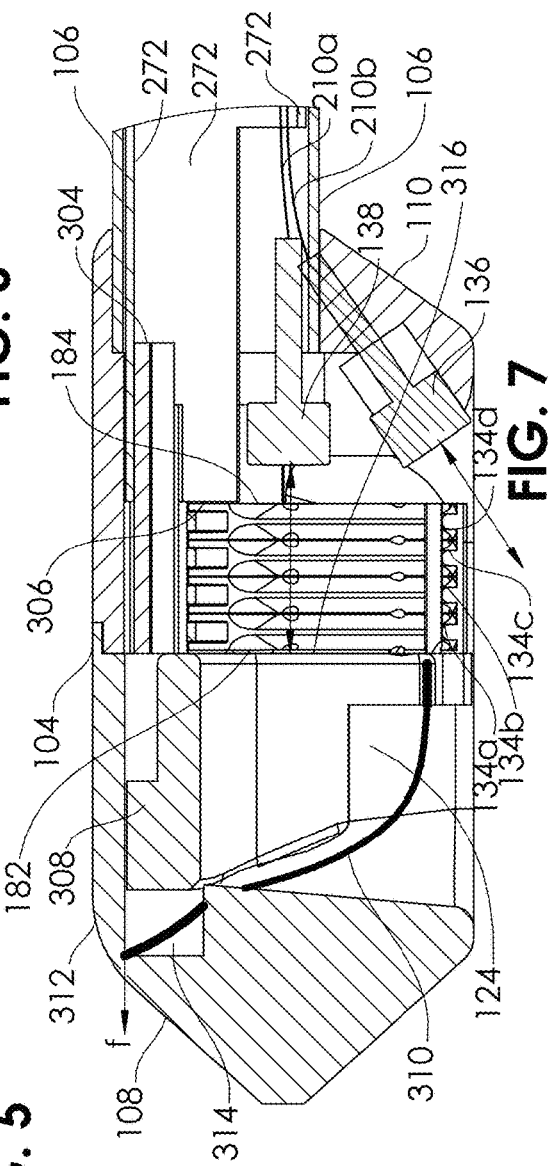

SYSTEMS AND METHODS FOR CLOSING PORTIONS OF BODY TISSUE

INCORPORATION BY REFERENCE TO ANY PRIORITY APPLICATIONS

This application claims the benefit of priority to U.S. Provisional Application No. 62/460,837, filed on Feb. 19, 2017, which is herein incorporated by reference in its entirety for all purposes. Priority is claimed pursuant to 35 U.S.C. § 119.

BACKGROUND OF THE INVENTION

Field of the Invention

The field of the invention generally relates to a system for closing or modifying tissue in the body of a subject. Such tissue may include one or more blood vessels, such as a hemorrhoidal artery. More particularly, the present invention relates to methods and apparatus to treat hemorrhoids without subjecting patients to pain, or with minimal pain.

Description of the Related Art

Currently, several medical conditions require that a section of tissue be closed or ligated at a portion internal to the body of a subject. The location of the tissue may be within a naturally occurring duct, cavity, organ, or vessel of the body, or may be within an opening created in a surgical procedure.

SUMMARY OF THE INVENTION

In one embodiment of the present disclosure, a system for closing a blood vessel includes a housing having a proximal end and a distal end and configured to be held in the hand of a user, an elongate body extending from the distal end of the housing and configured for insertion into the rectum of a subject, a distal housing having a proximal end coupled to a distal end of the elongate body, and having a cavity communicating with an opening on a side of the distal housing, a lumen extending through the elongate body and communicating with the cavity of the distal housing, the lumen configured to couple to a vacuum source, a sensor carried by the distal housing at or adjacent the cavity and configured for identifying a blood vessel, and wherein the lumen is configured to allow the insertion and removal of a probe having a distally-located vessel closure module, and wherein the lumen is configured to maintain a vacuum within the cavity when the probe is within the lumen with the vessel closure module within the cavity.

In another embodiment of the present disclosure, a method for closing a blood vessel includes the steps of providing a system for closing a blood vessel including a housing having a proximal end and a distal end and configured to be held in the hand of a user, an elongate body extending from the distal end of the housing and configured for insertion into the rectum of a subject, a distal housing having a proximal end coupled to a distal end of the elongate body, and having a cavity therein, the cavity communicating with an opening on a side of the distal housing, a lumen extending through the elongate body and communicating with the cavity of the distal housing, the lumen configured to couple to a vacuum source, a sensor carried by the distal housing at or adjacent the cavity and configured for identifying a blood vessel, and wherein the lumen is further configured to allow the insertion and removal of a probe having a distally-located vessel closure module, and wherein the lumen is configured to maintain a vacuum within the cavity when the probe is within the lumen with the vessel closure module within the cavity, placing the distal housing within a internal structure of a subject, identifying at least partially with the sensor a blood vessel to be closed, inserting a first probe having a first vessel closure module into the lumen such that the first vessel closure module is at least partially within the cavity, coupling a vacuum source to the lumen, such that at least a portion of the blood vessel is pulled into the cavity, and at least partially closing the blood vessel with the first vessel closure module.

In still another embodiment of the present disclosure, a system for closing a blood vessel includes a clip having a first jaw and a second jaw, the first and second jaws configured to be movable with respect to each other between a closed state and an open state, each of the first and second jaws including a proximal end and a distal end, and having an aperture carried thereon and a first guiding feature at or adjacent the proximal end, wherein the clip is biased in the closed state, an elongate body configured for insertion adjacent a blood vessel within a subject, first and second pins, each pin having a first end coupled to the body and a free second end, the second end of the first pin and the second end of the second pin separated by a distance $d_2$, wherein the aperture of the first jaw of the clip is configured to be slidably carried by at least the second end of the first pin and the aperture of the second jaw of the clip is configured to be slidably carried by at least the second end of the second pin, such that the clip is held in its open state, second and third guiding features carried by the body, the second guiding feature configured to interface with the first guiding feature of the first jaw of the clip and the third guiding feature configured to interface with the first guiding feature of the second jaw of the clip, and a displacement element movably coupled to the body and configured to change the relative displacement between the clip and the first and second pins in a first direction, so as to cause the aperture of the first jaw to disassociate with the second end of the first pin and the aperture of the second jaw to disassociate with the second end of the second pin allowing the clip to move towards its closed state, wherein movement of the clip towards its closed state causes the first guiding features of the first and second jaws to interface with the second and third guiding features to move the clip in relation to the body in a second direction different from the first direction.

In yet another embodiment of the present disclosure, a system for closing a blood vessel includes a clip having a first jaw and a second jaw, the first and second jaws configured to be movable with respect to each other between a closed state and an open state, each of the first and second jaws including a proximal end and a distal end, and having an aperture carried thereon and a first guiding feature at or adjacent the proximal end, wherein the clip is biased in the closed state, an elongate body configured for insertion adjacent a blood vessel within a subject, first and second pins, each pin having a first end coupled to the body and a free second end, the second end of the first pin and the second end of the second pin separated by a distance $d_2$, wherein the aperture of the first jaw of the clip is configured to be slidably carried by at least the second end of the first pin and the aperture of the second jaw of the clip is configured to be slidably carried by at least the second end of the second pin, such that the clip is held in its open state, second and third guiding features carried by the body, the second guiding feature configured to interface with the first guiding feature of the first jaw of the clip and the third guiding feature configured to interface with the first guiding feature of the second jaw of the clip, and a displacement element movably coupled to the body and configured to change the relative displacement between the clip and the first and second pins in a first direction, so as to cause the aperture of the first jaw to disassociate with the second end of the first pin and the aperture of the second jaw to disassociate with the second end of the second pin allowing the clip to move towards its closed state, wherein movement of the clip towards its closed state is at least temporarily controlled by the interface between the second and third guiding features with the first guiding features of the first and second jaws, such that a distance between the distal ends of the first and second jaws decreases at a faster rate than a distance between the proximal ends of the first and second jaws.

In still another embodiment of the present disclosure, a system for closing a blood vessel includes a housing having a proximal end and a distal end and configured to be held in the hand of a user, an elongate body extending from the distal end of the housing and configured for insertion adjacent a blood vessel within a subject, a distal housing having a proximal end coupled to a distal end of the elongate body, and having a cavity contained therein, the cavity including an opening on a side of the distal housing, a lumen passing through the elongate body and terminating at the cavity of the distal housing, the lumen configured to couple to a vacuum source, a sensor carried by the distal housing adjacent the cavity and configured for identifying a blood vessel, and wherein the lumen is configured to allow the insertion and removal of a probe having a vessel closure module carried at its distal end, and wherein the lumen is configured to maintain a vacuum within the cavity when the probe is within the lumen and the vessel closure module is within the cavity.

In yet another embodiment of the present disclosure, a method for closing a blood vessel includes providing a system including a housing having a proximal end and a distal end and configured to be held in the hand of a user, an elongate body extending from the distal end of the housing and configured for insertion adjacent a blood vessel within a subject, a distal housing having a proximal end coupled to a distal end of the elongate body, and having a cavity contained therein, the cavity including an opening on a side of the distal housing, a lumen passing through the elongate body and terminating at the cavity of the distal housing, the lumen configured to couple to a vacuum source, wherein the lumen is configured to allow the insertion and removal of a probe having a vessel closure module carried at its distal end, and wherein the lumen is configured to maintain a vacuum within the cavity when the probe is within the lumen and the vessel closure module is within the cavity, and a sensor carried by the distal housing adjacent the cavity and configured for identifying a blood vessel, placing the distal housing within an internal structure of a subject, identifying at least partially with the sensor a blood vessel to be closed, inserting a first probe having a first vessel closure module into the lumen such that the first vessel closure module is at least partially within the cavity, coupling a vacuum source to the lumen, such that at least a portion of the blood vessel is pulled into the cavity, and at least partially closing the blood vessel with the first vessel closure module.

BRIEF DESCRIPTION OF THE DRAWINGS

FIG. 4 is a block diagram of a clip application system according to an embodiment of the disclosure.

FIG. 5 is a view of the distal end of the clip application system.

FIG. 6 is a sectional view of the clip application system of FIG. 5, taken along line 6-6.

FIG. 7 is a detail view of the clip application system of FIG. 6, within circular area 7.

DETAILED DESCRIPTION OF THE ILLUSTRATED EMBODIMENTS

The present invention relates to a system for closing or modifying tissue in the body of a subject. The system may be configured for applying one or more clips to tissue in the body of a subject. The system may alternatively be configured to incorporate other modes for closing the tissue of the patient, which do not include clips. The system may be configured to close a blood vessel, such as a hemorrhoidal artery, and may include one or more sensors for identifying the blood vessel. The one or more sensors may include ultrasound sensors configured to use Doppler sensing. The system may include the controlled application of a vacuum to pull tissue into a distal housing, so that one or more clips may be applied to the tissue.

Figure 1:
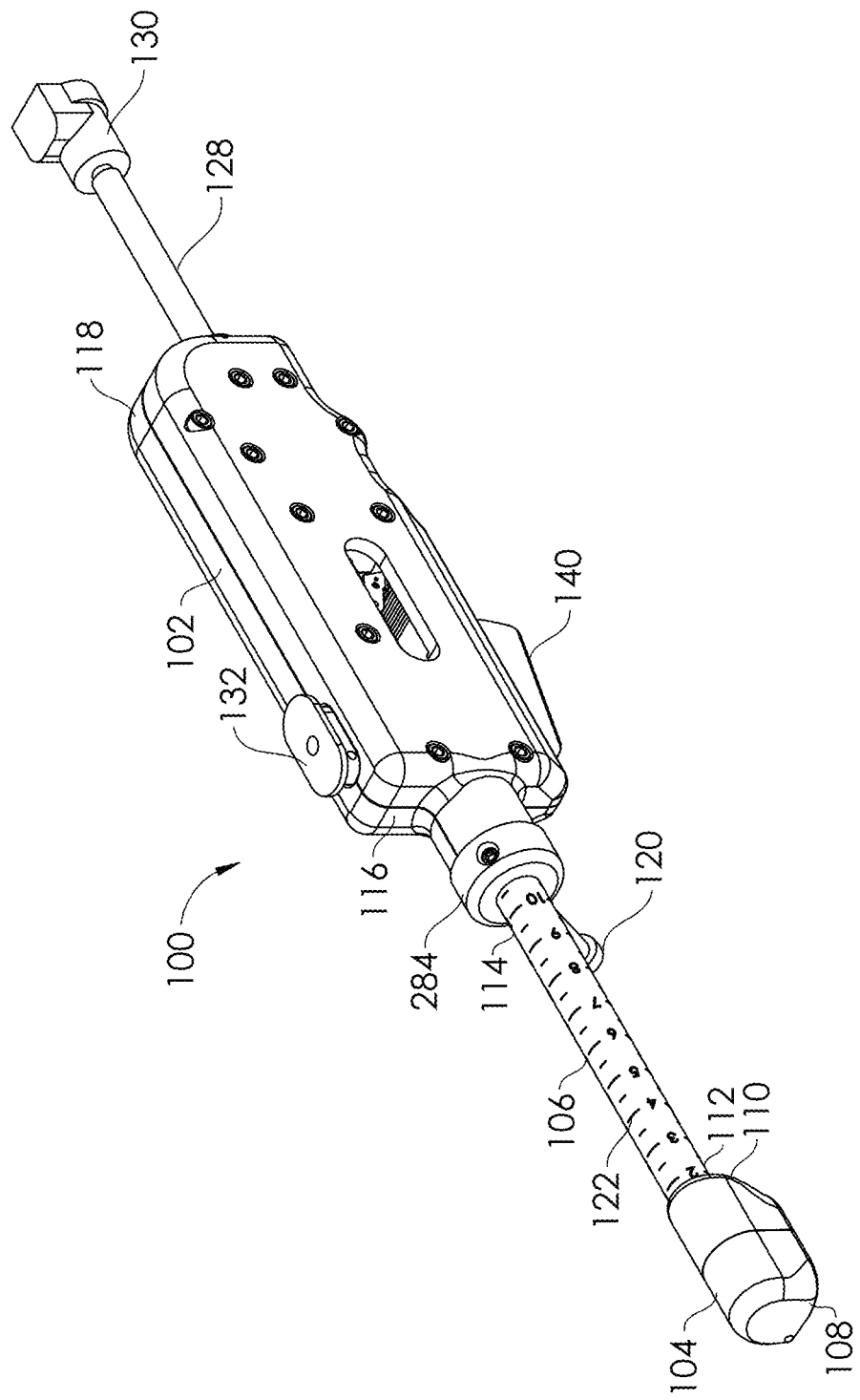
FIG. 1 is a perspective view of a clip application system according to an embodiment of the disclosure.

FIG. 1 illustrates a clip application system 100 according to an embodiment of the disclosure. The clip application system 100 includes a housing 102 which is coupled to a distal housing 104 via a tubular shaft 106. The distal housing 104 has a distal end 108 and a proximal end 110, and the tubular shaft 106 has a distal end 112 and a proximal end 114. The housing 102 also has a distal end 116 and a proximal end 118. The distal end 112 of the tubular shaft 106 is coupled to the proximal end 110 of the distal housing 104 and the proximal end 114 of the tubular shaft 106 is coupled to the distal end 116 of the housing 102. The distal housing 104 is configured to be placed within a natural or artificial opening, duct, cavity, vessel, or organ of the body of a subject, for example, a patient. The distal housing 104 is in some embodiments configured to be inserted into the anus and rectum of a subject, for placement adjacent a blood vessel, such as a hemorrhoidal artery. The housing 102 is configured to be gripped by one or both hands of an operator or user. In some embodiments, the housing 102 may be gripped by a first hand of the user and a transverse extension 120 may be gripped by the second hand of the user, thus allowing controlled rotation of the housing 102, tubular shaft 106, and distal housing 104. In other embodiments, as described further herein, the tubular shaft 106 and distal housing 104 may be rotated in relation to the housing 102. Either way, the transverse extension 120 may comprise a transverse or partially transverse rod, and may be used as a visual indicator of the rotational orientation status of the distal housing 104 in relation to a particular portion of tissue. One or more depth markings 122 may be printed, cut, etched or otherwise placed on the tubular shaft 106, in order to serve as a visual depth indicator. The depth markings 122 may be used to determine or estimate the inserted depth of the distal housing 104 within the body of the subject.

Figure 2:
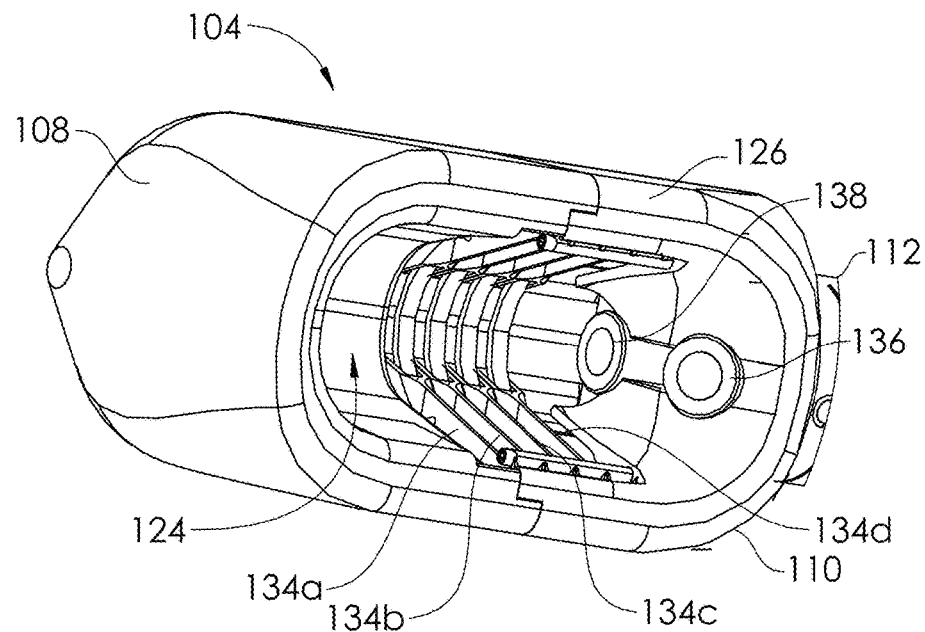
FIG. 2 is a detail view of the interior of a distal housing of the clip application system.

FIG. 2 illustrates an underside 126 of the distal housing 104, which includes a cavity 124 configured to engage tissue via a vacuum pathway, which will be described later. For the application of vacuum, a tubing 128 (FIG. 1) extends from the housing 102 and is coupled to a connector 130, which in turn is configured to be coupled to a vacuum source. A vacuum button 132 is carried on the housing 102 and may be operated by the hand of the user (e.g., by the thumb) in order to selectively apply a vacuum. One or more clips 134a-d are carried by the distal housing 104, and are deliverable therefrom. Two ultrasound Doppler sensors 136, 138, carried within the cavity 124, are shown in FIG. 2, but any number of sensors may be used, including one, two, three, or more. In an alternative embodiment, the Doppler sensor 136, 138 may be replaced by other types of sensors, including infra-red, near infra-red, optical coherence tomography (OCT), or optical fiber imaging. A first Doppler sensor 136 is shown oriented toward the underside 126 of the distal housing 104. This Doppler sensor 136 may be used, for example, to locate an artery to close with one or more of the clips 134a-d. A second Doppler sensor 138 is shown oriented towards the interior of the cavity 124, and may be used to judge the effect of clip placement over a tissue mass that has been pulled into the cavity 124. The second Doppler sensor 138 may also be used to determine whether a blood vessel, such as an artery, has been successfully closed by the one or more clips 134a-d. Returning to FIG. 1, a trigger 140 is movably coupled to the housing 102 and is configured to deliver the one or more clips 134a-d. In some embodiments, the vacuum button 132 is coupled to the trigger 140. For example, the trigger 140 may be configured to not function when the vacuum button 132 is not depressed, and to function only when the vacuum button 132 is depressed. As another example, the vacuum button 132 may unlock a locking feature (of the trigger 140) when the vacuum button 132 is depressed.

Figure 3A:
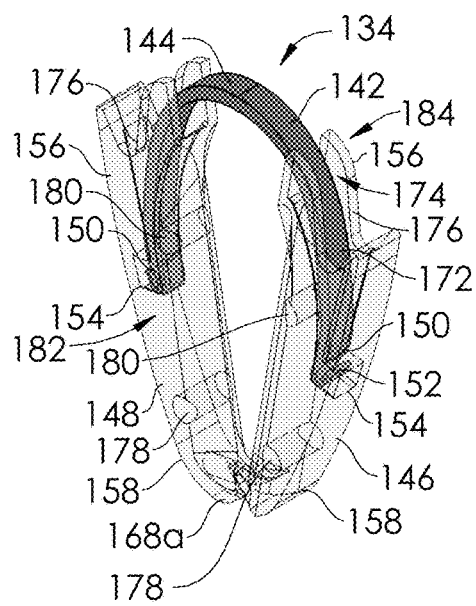
FIG. 3A is a perspective view of a clip according to an embodiment of the disclosure.
Figure 3B:
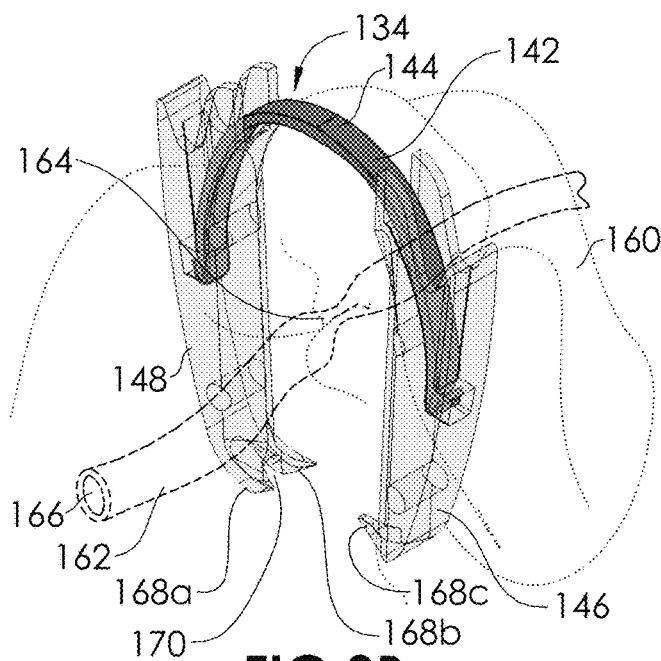
FIG. 3B is a perspective view of the clip of FIG. 3A applied to tissue of a patient to close a hemorrhoidal artery.

A clip 134 is illustrated in a substantially closed state in FIG. 3A and in a partially closed state in FIG. 3B. The clip 134 comprises a base 142 having a proximal portion 144 and two opposing jaws 146, 148. In some embodiments, the clip 134 comprises a base 142 that comprises a metallic material configured to provide a biasing force. The metallic material may comprise a superelastic or shape-memory material such as a nickel titanium alloy (Nitinol). The base 142 includes ends 150 having locking features 152, which may comprise a bent or curved end, as shown, or in alternative embodiments, an otherwise enlarged end (ball, bead, cap, etc.). The locking features 152 are configured to snap within respective snap cavities 154. The locking feature 152 may permanently snap into the snap cavity 154 (i.e., not be removable) or may releasably snap into the snap cavity 154. Each jaw 146, 148 has a proximal end 156 and a distal end 158. The base 142 may be biased in a manner such that the clip 134 is in a normally substantially closed state or condition, as in FIG. 3A, such that when it is delivered over tissue, it is self-closing. The clip 134 is shown in FIG. 3B compressing tissue 160 so as to close the lumen 166 of a hemorrhoidal artery 162 at an occlusion region 164. In some embodiments, the distal ends 158 of the jaws 146, 148 include teeth 168a-c, which may be configured to engage each other when the clip is in a substantially closed state (FIG. 3A). For example, tooth 168c may be configured to fit within a gap 170 between teeth 168a and 168b. As seen in FIG. 3B, when the clip 134 is in the partially closed state or condition, the tooth 168c may not fully engage with the teeth 168a, 168b, but the teeth 168a-c may still serve to engage the tissue 160, for example, to steady or secure the clip 134 and maintain it in place. Arms 172 extending from the proximal portion 144 of the base 142 toward the ends 150 may at least partially be guided or encased within channels 174 in the jaws 146, 148. The proximal end 156 of each jaw 146, 148 may include guiding features 176, which will be described in more detail herein. Apertures 178, 180 in the jaws 146, 148 are also shown in FIGS. 3A and 3B, and will described in more detail herein. The apertures 178, 180 may comprise holes, grooves, slits, cavities, channels, or other features, substantially extending between a first side 182 and a second side 184 of each jaw 146, 148. The apertures 178, 180 may comprise holes which extend through the jaws 146, 148, as shown in FIGS. 3A and 3B, or may instead extend along an internal or external exterior of the jaws 146, 148. The jaws 146, 148 may be formed of a large number of different metallic or polymeric materials, including stainless steel, nitinol, nylon, ABS or polycarbonate. Apertures 180 and/or 178 may be configured to allow releasable engagement with a loading tool (not shown), which is configured to load one or more of the clips 134 in to the distal housing 104. The loading tool may be a hand-held device which is configured to releasably carry one or more of the clips 134.

Returning to FIG. 2, the clips 134a-d are shown within the cavity 124 of the distal housing 104 in a forced-open state. The clip application system 100 is configured to release the clips 134a-d (e.g., one at a time) over tissue so that they move toward their substantially closed state due to the bias in the base 142.

The clip application system 100 is illustrated in FIG. 4 with the connector 130 coupled to a control unit 200 comprising a vacuum source 202 and a Doppler console 204. Though in alternative embodiments, the vacuum source 202 and Doppler console 204 may be separate, in FIG. 4, they are shown integrated into the single control unit 200. In alternative embodiments, the vacuum source 202 may simply comprise a lockable, medium or large bore syringe, a vacuum bottle, or a hospital or clinic vacuum line. The vacuum source 202 may include a vacuum pump which can be coupled to the connector 130. The connector 130 includes an electrical connector 206 to the Doppler console 204, shown connector via one or more conductors 208. Turning to FIGS. 5-7, the electrical connector 206 is electrically coupled to the Doppler sensors 136, 138 via one or more cables 210 which extend through the interior of the clip application system 100. The Doppler console 204 supplies voltage via battery or wall outlet-based electricity to power the Doppler sensors 136, 138, and in turn receives signals from the Doppler sensors 136, 138. The Doppler console 204 (FIG. 4) may include a control panel 212 for operating the Doppler console 204 and the Doppler sensors 136, 138. The Doppler console 204 may include multiple channels, for example a first channel configured to connect with the signals related to Doppler sensor 136 and a second channel configured to connect with the signals related to Doppler sensor 138. A switch 214 on the control panel 212 is used to switch between the first channel and the second channel. In some embodiments, the switch 214 is an automatic switch or relay, that activates and selects the Doppler sensor 138 automatically whenever the vacuum or suction is applied (e.g., by depression of the vacuum button 132). The word "vacuum" used herein is not intended to mean a theoretically complete vacuum (where no molecules are present), but rather a generally negative pressure. Any of the controls on the control panel may be hard wired mechanical switches, or touch sensitive, or even voice-controlled. A loudspeaker 216 is configured to allow a user to listen to audio feedback which is proportional to returned Doppler signals. The double-ended arrows in FIG. 7 represent the bi-directional travel of ultrasound signals. A display 218 may also be configured to indicate information related to the operation of the Doppler console 204. A separate display may be used to monitor the condition of the vacuum source 202, or the display 218 itself may be configured to include this information.

Figure 8:
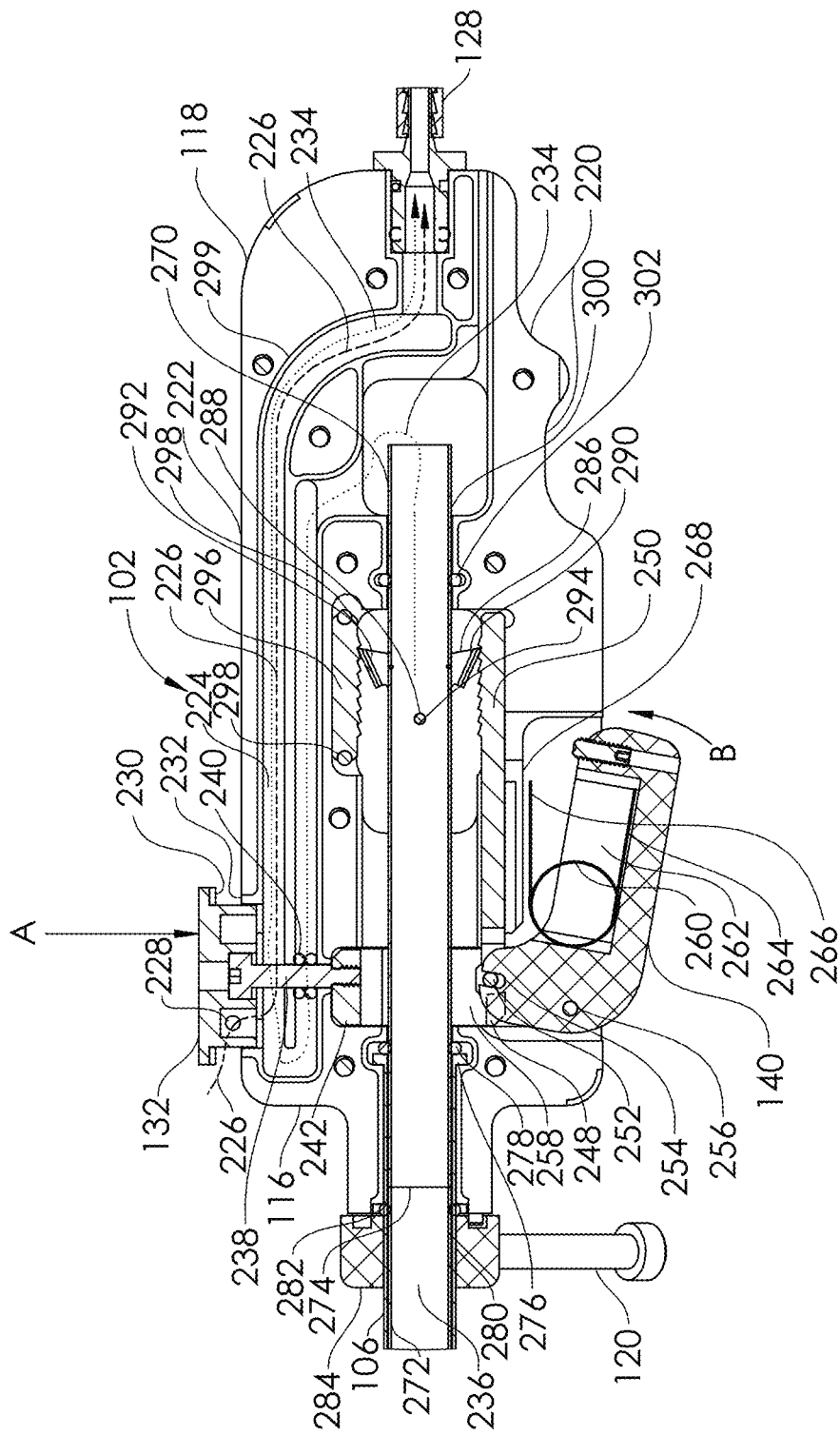
FIG. 8 is a detail view of the clip application system of FIG. 6, within oval area 8.

FIG. 8 illustrates a detailed sectional view of the housing 102 and its components. Grips 220 on the exterior of the housing 102 are configured to allow the housing 102 to be gripped easily by the user's hand. In one gripping style, the user's palm is wrapped around an upper portion 222 of the housing, and one to three fingers are engaged with the grips 220. The user is now able to maintain the position of the housing 102, while having access to the vacuum button 132 with the thumb and to the trigger 140 with the index finger and/or other finger. With the connector 206 (FIG. 4) coupled to the vacuum source 202, and with the vacuum button 132 in a non-depressed state, as shown in FIG. 8, air surrounding the housing 102 is continuously aspirated into an opening 228 in the vacuum button 132 and into a vacuum channel 224 via pathway 226 (dashed line). Thus, no significant vacuum is applied to the cavity 124 of the distal housing 104. In use, the clip application system 100 may be inserted in this condition by the user into a duct, tract, etc. in the body of the subject and manipulated such that the cavity 124 of the distal housing 104 is placed in a desired location, for example, adjacent an artery. The switch 214 of the Doppler console 204 (FIG. 4) may be operated to assure that a particular Doppler sensor (e.g., Doppler sensor 136) is selected to sense the location of an artery which is desired for closure/occlusion. Then the desired location including target tissue is identified, the user may manipulate the housing using the transverse extension 120 and/or the depth markings 122 to rotate and or longitudinally displace the distal housing 104 so that the cavity 124 is adjacent the target tissue.

Figure 10A:
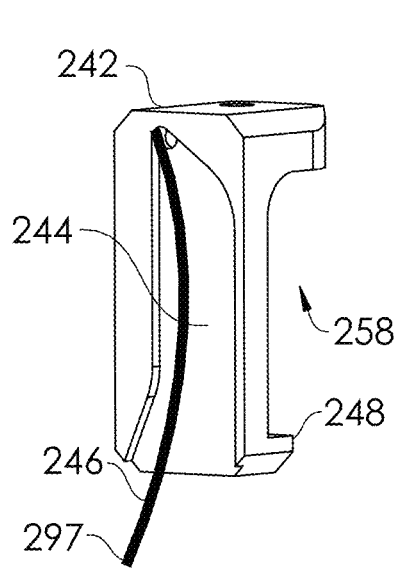
FIG. 10A is a perspective view of a locking element of the clip application system in a first position according to an embodiment of the disclosure.
Figure 10B:
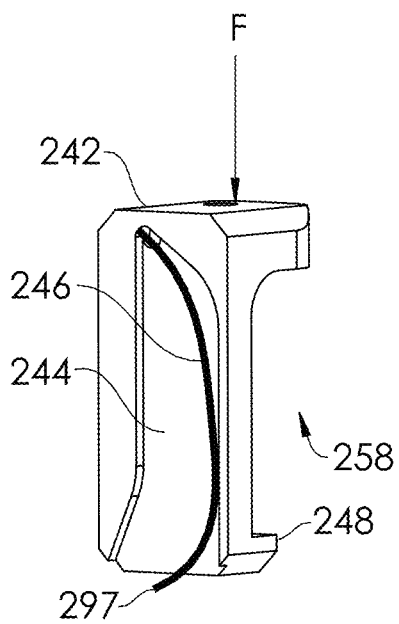
FIG. 10B is a perspective view of the locking element in a second position.

When the user desires to apply vacuum to force the target tissue into the cavity 124 of the distal housing 104, the user depresses the vacuum button 132 in direction A, causing a perimeter seal 230 coupled to the vacuum button 132 to seal onto the surface 232 of the housing 102. The perimeter seal 230 may comprise an o-ring, a gasket, or any other type of seal that effectively closes the external access of the opening 228. With the vacuum button 132 depressed and the perimeter seal 230 engaging the surface 232 of the housing 102, a vacuum is now applied to the cavity 124 of the distal housing 104, as shown in pathway 234 (dotted line) via the lumen 236 of the tubular shaft 106. Also, when the vacuum button 132 is depressed in direction A, a connecting element 238, secured to the vacuum button 132, is also displaced in direction A. One or more o-ring seals 240, or other seals, seal around the connecting element 238 to prevent unwanted internal leak paths. The connecting element 238 is secured to a locking member 242 which is thus also moved in the direction A. The outside of the locking member 242 is shown in FIGS. 10A and 10B, and includes an indentation 244 into which is fit a spring member 246. The spring member 246 extends within the indentation 244, and engages the housing 102 at its extreme end 297. The spring member 246 has a slight curve in its unstressed configuration (FIG. 10A), and will selectively bow (FIG. 10B) when a force F is placed on the locking member 242 (via the vacuum button 132 and the connecting element 238). Thus, the spring member 246 will cause the locking member 242 to return to the position of FIG. 10A when finger pressure is released from the vacuum button. When the vacuum button 132 is not depressed, an abutment 248 of the locking member 242 blocks longitudinal displacement of a first rack 250. The trigger 140 is attached in a cam relationship to the first rack 250 with a pin 252 of the first rack 250 engaging a slot 254 of the trigger 140. Pivot pin 256 rotatably couples the trigger 140 to the housing 102. Thus, when the abutment 248 of the locking member 242 blocks the longitudinal displacement of the first rack 250, the first rack 250 in turn blocks movement of the trigger 140. Thus, the trigger 140 is incapable of delivering any clips 134a-d unless a vacuum is applied to the cavity 124 of the distal housing 104 (via the depression of the vacuum button 132). This helps prevent any clips 134a-d being delivered when tissue is not pulled within the cavity 124 of the housing 104, thus increasing safety of the procedure.

When the user depresses the vacuum button 132 and thereby moves the abutment 248 of the locking member 242 to a position below the first rack 250, the longitudinal displacement of the first rack 250 is no longer blocked, as a relief 258 in the locking member 242 is now positioned adjacent the first rack 250. Thus, the user is now capable of depressing the trigger 140 in direction B (in relation to the pivot pin 256) to deliver one or more clips 134a-d, as will be described later. A spring 260 is contained in a recess 262 in the trigger 140, and has a first arm 264 which engages the trigger 140 and a second arm 266 which engages a surface 268 of the housing 102. Thus, when the user releases the depressed trigger 140, the trigger moves in a direction opposite of direction B, and returns to its original position. Referring to both FIG. 7 and FIG. 8, a proximal inner pushing tube 270 abuts a distal inner pushing tube 272 at an abutment location 274 within the tubular shaft 106, such that distal longitudinal movement (to the left in FIG. 8) of the proximal inner pushing tube 270 will push the distal inner pushing tube 272 in a distal direction within the tubular shaft 106. The proximal end 276 of the tubular shaft 106 is sealed within the housing 102 by a first o-ring 278, and an outer diameter surface 280 of the tubular shaft 106 is sealed with the housing 102 by a second o-ring 282, thus maintaining any vacuum applied within the tubular shaft 106 without leakage. The tubular shaft 106 is additionally bonded (adhesive, epoxy, welding, etc.) to the housing 102 so that the housing 102 and the tubular shaft 106 turn in unison. A distal cap 284 may be attached to the housing 102 in order to secure the tubular shaft 106 and its internal components together, and to allow them to be rotated (by virtue of the transverse extension 120) in relation to the housing 102. One of the distal cap 284 or the housing 102 may have a circumferentially extending male or female feature which is configured to engage with a female or male feature on the other of the distal cap 284 or the housing 102. For example, the distal cap 284 may include a circumferentially extending slot or groove and the housing 102 may include a pin that is configured to slide within the circumferentially extending groove. In some embodiments, the circumferentially extending groove extends less than a full rotation. For example, the groove may extend between about 180° and 355°, or between about 270° and about 355°, or between about 330° and about 355°. This final example allows almost a complete rotation of the distal housing 104 in relation to the housing 102. The proximal inner pushing tube 270 is coupled to a spring-loaded dual pawl 286 having a pin 288, a first pawl 290, and a second pawl 292. The spring-loaded dual pawl 286 may be constructed from a superelastic material (Nitinol, nickel titanium alloy). The pin 288 is inserted through a transverse hole 294 in the proximal inner pushing tube 270 so that the two pawls 290, 292 longitudinally displace in unison with the proximal inner pushing tube 270.

Figure 9:
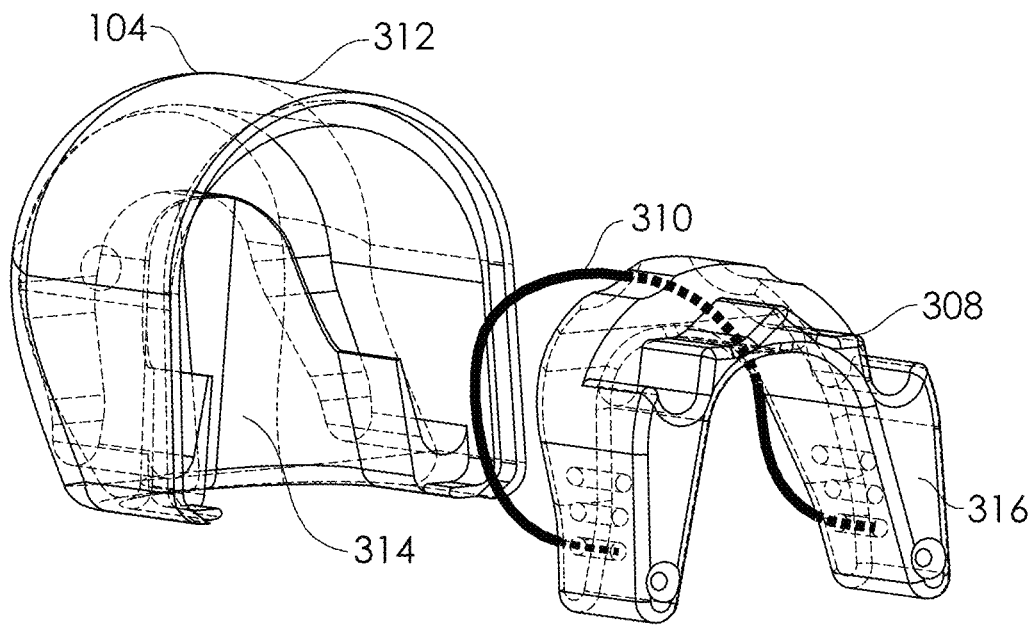
FIG. 9 is an exploded view of a blocking member within a distal end of the distal housing of the clip application system.
Figure 11:
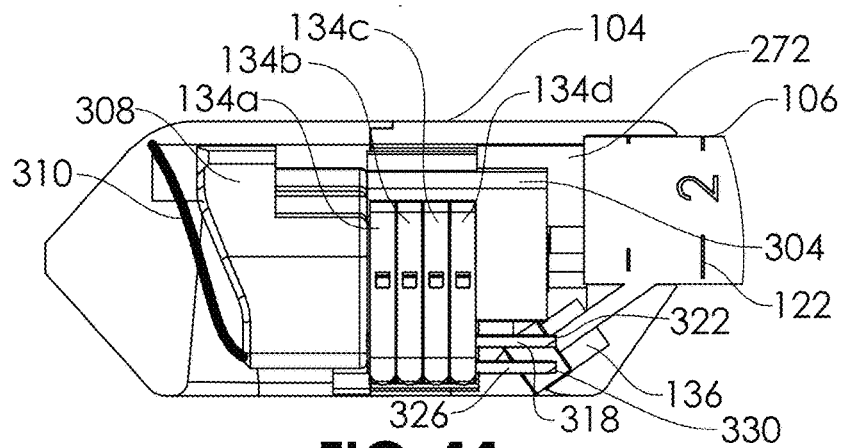
FIG. 11 is a sectional view of the distal housing of the clip application system prior to actuating a clip.

With the vacuum button 132 depressed and the desired tissue sucked into the cavity 124 of the distal housing 104 (which may be confirmed via the Doppler sensor 138), the user depresses the trigger 140 causing the first rack 250 to be moved distally. Movement of the first rack 250 in this distal direction causes engagement with the end of the first pawl 290 thus moving the first pawl 290 distally and, via engagement of the pin 288 in the transverse hole 294, also causing the proximal inner pushing tube 270 to be moved distally. A second rack 296 is rigidly secured to the housing 102 with first and second pins 298. As the first rack 250, the first pawl 290, and the proximal inner pushing tube 270 move distally, the second pawl 292 repeatedly slips (ratchets) over the second rack 296. The exterior surface 300 of the proximal inner pushing tube 270 is dynamically sealed to the housing 102 by an o-ring 302. As depicted in FIG. 8, the housing 102 is a clamshell design with two halves, and may include multiple gaskets 299 (or alternatively, adhesive, epoxy, or vacuum grease lines) to maintain vacuums within channels such as vacuum channel 224. The proximal inner pushing tube 270 thus pushes the distal inner pushing tube 272 distally within the tubular shaft 106. As shown in FIG. 7, the distal inner pushing tube 272 is bonded or molded to a frame 304. Alternatively, the contours and features of the frame 304 may be integral to the distal inner pushing tube 272. Still alternatively, the contours and features of the frame 304 may be separate from the distal inner pushing tube 272, and may be, for example, carried within the distal housing 104. A distal surface 306 on the distal inner pushing tube 272 abuts a proximal side 184 of the proximal clip 134d. As the distal inner pushing tube 272 moves distally in relation to the distal housing 104, the distal surface 306 pushes the proximal clip 134d which thus pushes the other clips 134c, 134b, 134a in a stack distally. Referring also to FIG. 9, a spring-loaded block 308 having a spring wire 310 extending therefrom is telescopically displaceable within a distal portion 312 of the distal housing 104. Initially, the spring wire 310 produces a biasing force f (FIG. 7) against the interior 314 of the distal portion 312 of the distal housing 104 which forces the proximal surface 316 of the spring-loaded block 308 against a distal side 182 of the distal clip 134a. This thus forces the apertures 178 (FIG. 3A) in the jaws 146, 148 of the entire stack of clips 134a-d to remain on pins 318, 320 (FIGS. 11-13) which extend from the housing 102. The proximal ends 322 of each pin 318, 320 are secured to the housing 102, while the distal ends 324 are free.

Figure 12:
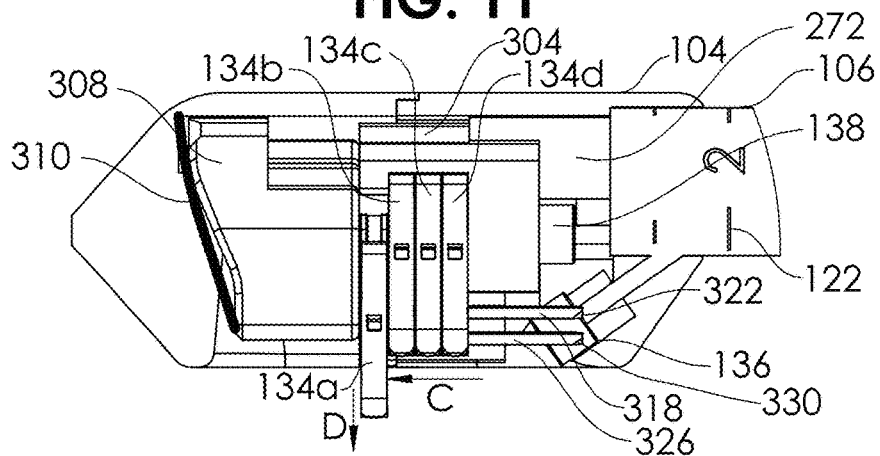
FIG. 12 is a sectional view of the distal housing of the clip application system upon actuating a clip.
Figure 13:
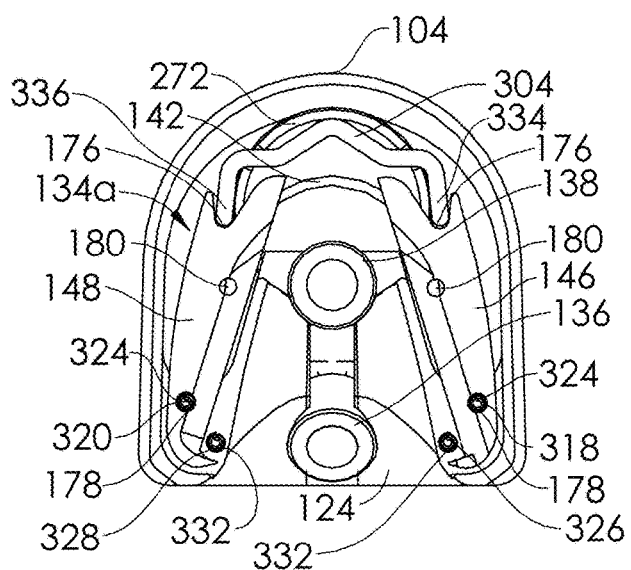
FIG. 13 is a cross-sectional view of the distal housing of the clip application system showing the location of the distal clip prior to actuating the distal clip.

When the distal clip 134a is forced off of the distal ends 324 of the pins 318, 320 by the forward displacement of the distal surface 306 of the distal inner pushing tube 272, the distal side 182 of the distal clip 134a pushes against the proximal surface 316 of the spring-loaded block 308, thus forcing it forward into the interior 314 of the distal portion 312 of the distal housing 104 against the biasing force of the spring wire 310. Thus, the clips 134a-d and the spring-loaded block 308 are moved from the position illustrated in FIG. 11 to the position illustrated in FIG. 12. The distal clip 134a in FIG. 12 is able to exit the cavity 124 of the distal housing 104. Additionally, a pair of pins 326, 328 extend from the housing 102. The proximal ends 330 of each pin 326, 328 are secured to the housing 102, while the distal ends 332 are free. As shown in FIG. 13, the pins 326, 328 are not configured to pass through any aperture in the jaws 146, 148, but instead are configured to protect the teeth 168a-c of the jaws (FIG. 3B) and/or to protect tissue from being lacerated or punctured by the teeth 168a-c when the tissue is drawn into the cavity 124 of the distal housing 104 (e.g., by vacuum). In some embodiments, a pin 326, 328 may have a diameter or transverse dimension d which is greater than or approximately equal to a profile thickness p of the tooth (or other feature). In some embodiments, the distal ends 332 of the pins 326, 328 are at the same longitudinal extension (location) as the distal ends 324 of the pins 318, 320. Thus, when a clip 134 is pushed off of the pins 318, 320, the clip 134 is also longitudinally cleared from the pins 326, 328, allowing the clip to move from the cavity 124 of the distal housing 104, as clip 134a does in FIG. 12, in generally perpendicular direction D.

Figure 14:
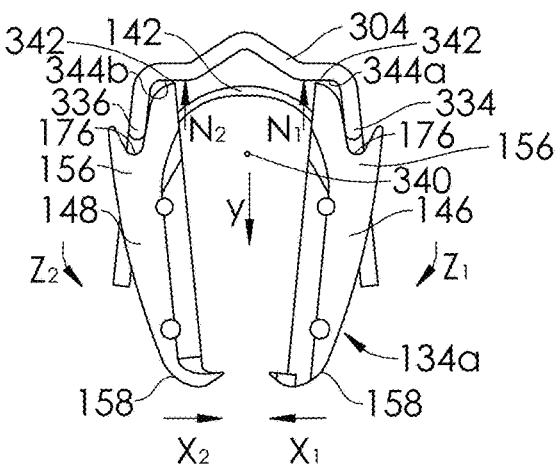
FIG. 14 is an isolated view of the distal clip in relation to guiding features, according to an embodiment of the disclosure.

The clip 134a is pushed longitudinally (direction C in FIG. 12), causing it to clear the ends 324, 332 of the pins 318, 320, 326, 328 and then move in the generally perpendicular direction D. This is demonstrated by FIG. 13, which shows the clip 134a immediately prior to being pushed off of the ends 324, 332 of the pins 318, 320, 326, 328, and FIG. 14, which shows the clip 134a immediately after it has been pushed off of the ends 324, 332 of the pins 318, 320, 326, 328, and as it is being guided by guiding features 334, 336 of the frame 304. In FIG. 14, only the clip 134a and the frame 304 are depicted, in order to better demonstrate their dynamic relationship. In FIG. 13, prior to the release of the clip 134a, the pins 318, 320 hold the jaws 146, 148 such that the guiding features 176 are deeply engaged with the guiding features 334, 336 of the frame 304. When the clip 134a is released, as in FIG. 14, the base 142 begins to close, which brings the distal ends 158 of the jaws 146, 148 toward each other (arrows $X_1$, $X_2$). The guiding features 334, 336 momentarily maintain a separation between the proximal ends 156 of the jaws 146, 148, even as the clip 134a begins to move or eject (arrow y) in relation to the frame 304 (and in relation to the distal housing 104). Thus, the jaw 146 rotates in one direction (arrow $Z_1$) in relation to the longitudinal axis 340 and the jaw 148 rotates in a substantially opposite direction (arrow $Z_2$) in relation to the longitudinal axis 340. The rotational movement of each jaw 146, 148 causes a proximal tip 342 of each jaw 146, 148 to contact a bottom surface points 344a-b with normal force vectors ($N_1$, $N_2$). The summation of normal force vectors $N_1$ and $N_2$ has a net direction substantially equivalent to the direction of arrow y, thus ejecting the clip 134a away from the frame 304, and hence, away from the distal housing 104. Because the guiding features 334, 336 initially maintain a separation between the proximal ends 156 of the jaws 146, 148 while the distal ends 158 are closing, the clip 134a is able to more reliably embrace or encircle the target tissue that is within the cavity 124 of the distal housing 104, as the clip 134a begins it ejection. This better ensures sufficient closure of the tissue and of any blood vessel that is within the tissue mass. Any of the guiding features 176, 334, 336 of the jaws 146, 148 or frame 304 may have a curvilinear shape so that, for example, the motion of the clip is not abrupt and/or does not have too much friction or other resistance. In some embodiments, any of the guiding features 176, 334, 336 may include a recess and or a protrusion.

Returning now to FIG. 8, once the clip 134a is applied by depressing trigger 140, the user then releases the trigger 140, which returns back to its initial position via the biasing of the spring 260. As the spring 260 forces the trigger 140 back to its initial, biased, position, the engagement of the pin 252 of the first rack 250 and the slot 254 of the trigger 140 causes the first rack 250 to move proximally (in a negative longitudinal direction). Because the proximal inner pushing tube 270 and the spring-loaded dual pawl 286 cannot move backwards (proximally) in relation to the second rack 296, instead, the first pawl 290 ratchets over the teeth (one or more tooth) of the first rack 250. The user may now repeat the steps described either deliver the next clip 134b into the same tissue mass, or to release the vacuum button 132 and move the distal housing 104 to a different location, then repeating the application of a vacuum, and the delivery of the next clip 134b. The ratcheting of the spring-loaded dual pawl 286 with the first rack 250 and the second rack 296 allows multiple clips to be applied in succession. The blocking of the most distal clip 134 at the ends 324, 332 of the pins 318, 320, 326, 328 by the action of the spring-loaded block 308 having a spring wire 310 assures that only one clip 134 is delivered at a time. In some embodiments, pin 318 and pin 320 are substantially parallel to each other, so that the clips 134 maintain a particular angular orientation between the two jaws 146, 148 the entire time that the clips 134 are slid along or over the pins 318, 320. In other embodiments, pin 318 and pin 320 diverge, in other words, the distance between them increases towards their distal ends 324. Thus, the clips 134 are caused to become more and more open as they are pushed distally along the pins 318, 320. In other embodiments, pin 318 and pin 320 converge, in other words, the distance between them decreases towards their distal ends 324. Thus, the clips 134 are caused to become less and less open as they are pushed distally along the pins 318, 320. Any of these configurations may be used for different purposes, such as to make more space in the outer portion of the distal housing 104 in its proximal end, to make more space in the inner portion of the distal housing in its proximal end, or to actively actuate the clip 134 (either increasing or decreasing its angle), which may be done to assure that it is not stuck in any one position.

In some embodiments, the pins 318, 320 are configured to hold only one clip 134. In other embodiments, the pins 318, 320 are configured to hold two or more clips, for example two to ten clips, or four clips, as depicted herein. Each pin 318, 320 may have a free portion length L and each clip 134 may have a thickness t (from side 182 to side 184). Thickness t may in some cases be the maximum thickness of the clip 134. In some embodiments, free portion length L is greater than thickness t, so as to fit at least one clip. In some embodiments, free portion length L is at least twice thickness t, so as to fit at least two clips. In some embodiments, free portion length L is at least three times thickness t, so as to fit at least three clips. In some embodiments, free portion length L is at least four times thickness t, so as to fit at least four clips. In some embodiments, free portion length L is at least five times thickness t, so as to fit at least five clips.

Many of the elements of the clip application system 100, including the housing 102 and distal housing 104, may comprise a number of polymeric materials, which may be formed from a variety of materials including polycarbonate or acrylonitrile butadiene styrene (ABS). The components of the housing 102 and distal housing 104 may be injection molded, blow molded, rotational molded, or may be machined, such as by CNC machining. Other components of the clip application system 100 may be formed from stainless steel, such as 300 series, or more specifically, 302 or 304 stainless steel. O-rings or seals may comprise Buna-N, EPDM, EPR, silicone, or other elastomers and thermoplastic elastomers.

Figure 15:
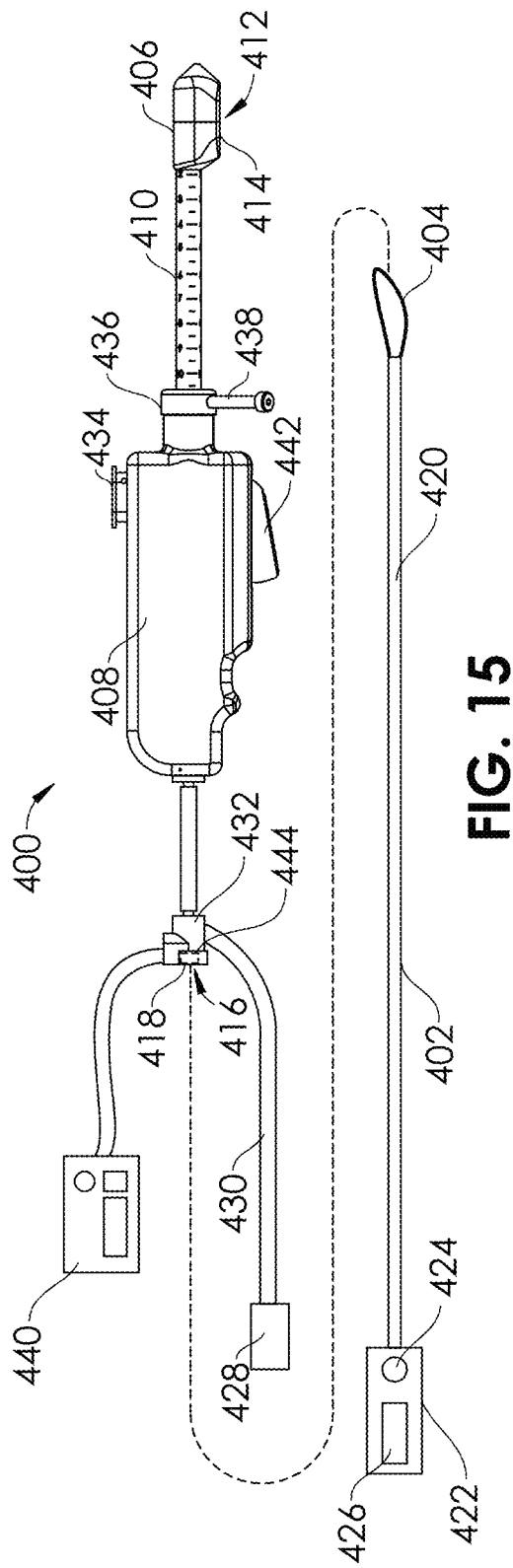
FIG. 15 is an elevation view of a system for closing a blood vessel according to an embodiment of the disclosure.
Figure 16:
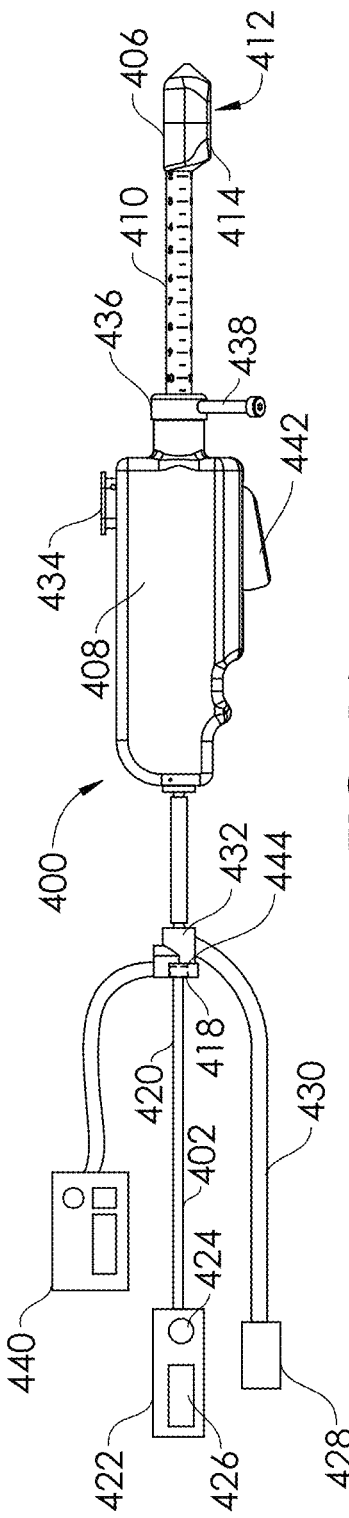
FIG. 16 is an elevation view of the system of FIG. 15 in use.

All of the embodiments described herein may be replaced by similar devices that incorporate cauterization, ligation, or staples, among other modalities, in conjunction with, or instead of the clips 134. A system for closure of a blood vessel 400 is illustrated in FIGS. 15-16 according to an embodiment of the disclosure. A housing 408 is coupled to a tubular shaft 410, which is coupled to a distal housing 406. The distal housing 406 includes a cavity 412 having an opening 414 at the side of the distal housing 406. A lumen 416 (e.g., channel) extends between a proximal opening 418 and the opening 414 in the distal housing 406. The lumen 416 is configured for accommodating placement of one or more probes 402, each having a shaft 420 with a vessel closure module 404 at its distal end. In FIG. 15, the vessel closure module 404 comprises a looped wire configured for cauterizing a mass of tissue, including a blood vessel. Other cautery elements may replace the looped wire in other embodiments, such as a pair of opposing jaws. These may include monopolar or bipolar driven elements. The probe 402 may be controlled via a control module 422, which includes an operational switch 424 (e.g., "cautery off/cautery on" via a toggle, slide, or other modality) and a display 426. As with the other embodiments presented herein, a vacuum source 428 is configured to be coupled to the cavity 412 of the distal housing 406, in this case, via the lumen 416. An extension tube 430 couples the vacuum source 428 to the lumen 416 via a connector 432. A vacuum is applied by a vacuum button 434 which is operable by the hand of a user. The distal housing 406 may be rotated along with the tubular shaft 410 by rotating a distal cap 436 and transverse extension 438. In embodiments that incorporate one or more Doppler sensors, a Doppler console 440 (which may be similar to Doppler console 204) is coupled to the Doppler sensor(s) via the connector 432. A spring-loaded lever 442 may be carried by the housing 408, to aid in the advancement of the probe 402, for example, by the repetitive, longitudinally-directed frictional engagement of the shaft 420. For example, each time the lever 442 is depressed, the shaft 420 is frictionally engaged and the shaft 420 is advanced distally a particular finite longitudinal distance in relation to the housing 408 and tubular shaft 410. The release of the lever 442, because it undoes the frictional engagement with the shaft 420, does not move the shaft 420 longitudinally. The connector 432 includes a seal 444 which may be configured in several different manners. First, the seal 444 may be a permanent seal, such as a duckbill valve or spring-activated valve, so that the proximal opening 418 is closed (sealed) when no probes 402 are within the lumen 416, and so that the proximal opening 418 seals around the diameter of the shaft 420 when the probe 402 is within the lumen. Alternatively, the seal 444 may be configured to seal only when the probe 402 is within the lumen, and may comprise an o-ring, a Touhy-Borst or a spring-loaded valve. An introducer may be used to more easily insert the vessel closure module 404 of the probe 402 into the lumen 416.

FIG. 16 shows the probe 402 inserted into the lumen 416, and with the closure module 404 advanced so that it is within the cavity 412 of the distal housing 406. In use, the user applies a vacuum to the cavity 412 by pressing the vacuum button 434. The target tissue is pulled into the cavity 412 and the vessel closure module 404 is activated. For example, the tissue is cauterized, to close the blood vessel within the tissue (e.g., hemorrhoidal artery, etc.). If more than one vessel closure module 404 needs to be applied to the tissue (or to more than one portion of the tissue), then the probe 402 may be removed from the lumen 416, and another probe 402 may be advanced through the lumen 416, with the treatment steps repeated. This may be repeated with any number of different probes 402, including probes of more than one modality (cautery, clip, staple, ligator, etc.). The housing 408/tubular shaft 410/distal housing 406 thus together can, in some cases, maintain a particular position adjacent to target tissue, while a number of different probes 402 can quickly and easily be advanced, applied, and removed in succession, to fully treat the target tissue. The speed of the procedure can thus be increased, because the distal housing 406 does not have to be readvanced or repositioned. Additionally, the sizes of the tubular shaft 410 and distal housing 406 can be reduced, for easier passage through body tracts or cavities, as they only need to accommodate a single probe 402 or vessel closure module 404 at a time, and not fit multiple probes or modules.

The system for closure of a blood vessel 400 is depicted as a cautery device, but in alternative embodiments the vessel closure module 404 may instead comprise a clamp, or clip that is deliverable from the distal housing 406, or a suture, ligation structure, or staple.

Figure 17:
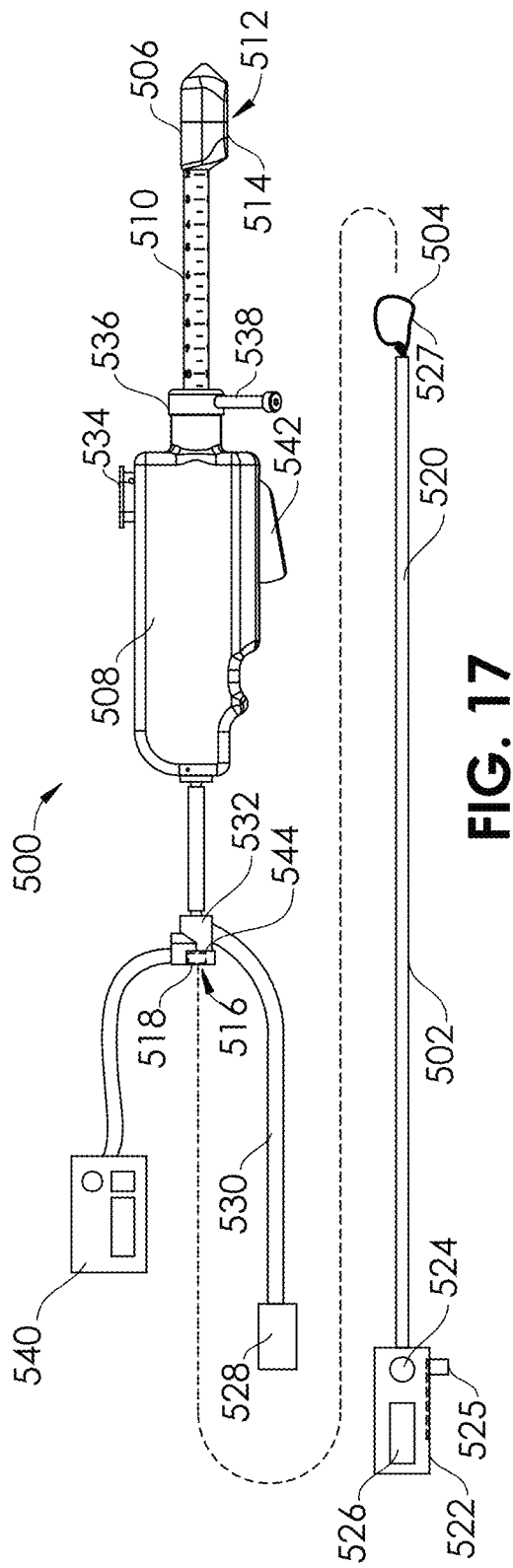
FIG. 17 is an elevation view of a system for closing a blood vessel according to an embodiment of the disclosure.
Figure 18:
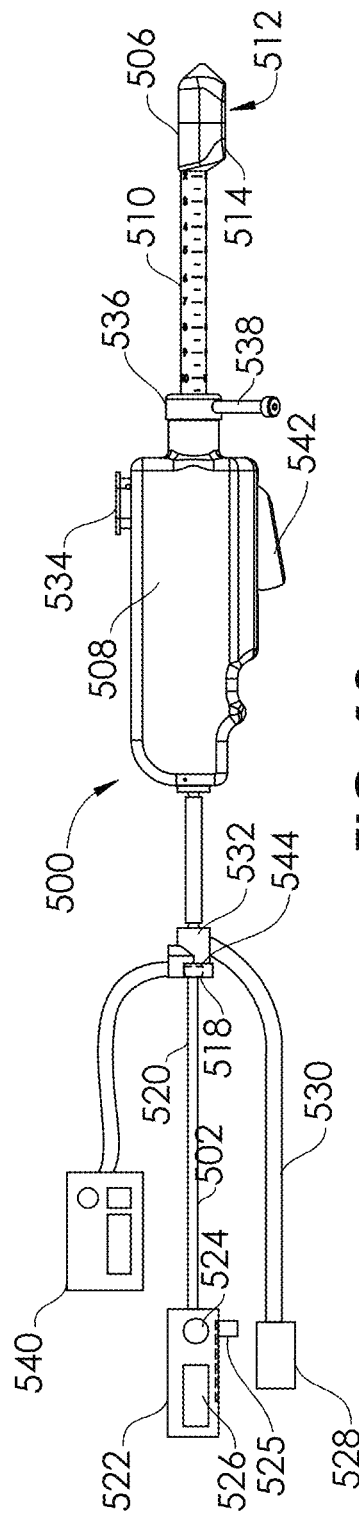
FIG. 18 is an elevation view of the system of FIG. 17 in use.

A system for closure of a blood vessel 500 is illustrated in FIGS. 17-18 according to an embodiment of the disclosure. A housing 508 is coupled to a tubular shaft 510, which is coupled to a distal housing 506. The distal housing 506 includes a cavity 512 having an opening 514 at the side of the distal housing 506. A lumen 516 (e.g., channel) extends between a proximal opening 518 and the opening 514 in the distal housing 506. The lumen 516 is configured for accommodating placement of one or more probes 502, each having a shaft 520 with a vessel closure module 504 at its distal end. In FIG. 17, the vessel closure module 504 comprises a ligation band for ligating a mass of tissue, including a blood vessel. Other ligation elements may replace the ligation band in other embodiments, such as string, wire, filament, fiber, or other tieable structures. The probe 502 may be controlled via a control module 522, which includes a switch 524 and/or a slide 525 and a display 526. The switch 524 may be configured to automatically cause a loop 527 of the ligation band (vessel closure module 504) to close, for example in a slip knot or noose-like manner. The slide 525 may also cause the loop 527 to close, but in a manual manner (by being slid by one or more fingers of the user's hand). As with the other embodiments presented herein, a vacuum source 528 is configured to be coupled to the cavity 512 of the distal housing 506, in this case, via the lumen 516. An extension tube 530 couples the vacuum source 528 to the lumen 516 via a connector 532. A vacuum is applied by a vacuum button 534 which is operable by the hand of a user. The distal housing 506 may be rotated along with the tubular shaft 510 by rotating a distal cap 536 and transverse extension 538. In embodiments that incorporate one or more Doppler sensors, a Doppler console 540 (which may be similar to Doppler console 204) is coupled to the Doppler sensor(s) via the connector 532. A spring-loaded lever 542 may be carried by the housing 508, to aid in the advancement of the probe 502, for example, by the repetitive, longitudinally-directed frictional engagement of the shaft 520. For example, each time the lever 542 is depressed, the shaft 520 is frictionally engaged and the shaft 520 is advanced distally a particular finite longitudinal distance in relation to the housing 508 and tubular shaft 510. The release of the lever 542, because it undoes the frictional engagement with the shaft 520, does not move the shaft 520 longitudinally. The connector 532 includes a seal 544 which may be configured in several different manners. First, the seal 544 may be a permanent seal, such as a duckbill valve or spring-activated valve, so that the proximal opening 518 is closed (sealed) when no probes 502 are within the lumen 516, and so that the proximal opening 518 seals around the diameter of the shaft 520 when the probe 502 is within the lumen. Alternatively, the seal 544 may be configured to seal only when the probe 502 is within the lumen, and may comprise an o-ring, a Touhy-Borst or a spring-loaded valve. An introducer may be used to more easily insert the vessel closure module 504 of the probe 508 into the lumen 516.

FIG. 18 shows the probe 502 inserted into the lumen 516, and with the closure module 504 advanced so that it is within the cavity 512 of the distal housing 506. In use, the user applies a vacuum to the cavity 512 by pressing the vacuum button 534. The target tissue is pulled into the cavity 512 and the vessel closure module 504 is activated. For example, the tissue is ligated, to close the blood vessel within the tissue (e.g., hemorrhoidal artery, etc.). If more than one vessel closure module 504 needs to be applied to the tissue (or to more than one portion of the tissue), then the probe 502 may be removed from the lumen 516, and another probe 502 may be advanced through the lumen 516, with the treatment steps repeated. This may be repeated with any number of different probes 502, including probes of more than one modality (cautery, clip, staple, ligator, etc.). The housing 508/tubular shaft 510/distal housing 506 thus together can, in some cases, maintain a particular position adjacent to target tissue, while a number of different probes 502 can quickly and easily be advanced, applied, and removed in succession, to fully treat the target tissue. The speed of the procedure can thus be increased, because the distal housing 506 does not have to be readvanced or repositioned. Additionally, the sizes of the tubular shaft 510 and distal housing 506 can be reduced, for easier passage through body tracts or cavities, as they only need to accommodate a single probe 502 or vessel closure module 504 at a time, and not fit multiple probes or modules.

Figure 19:
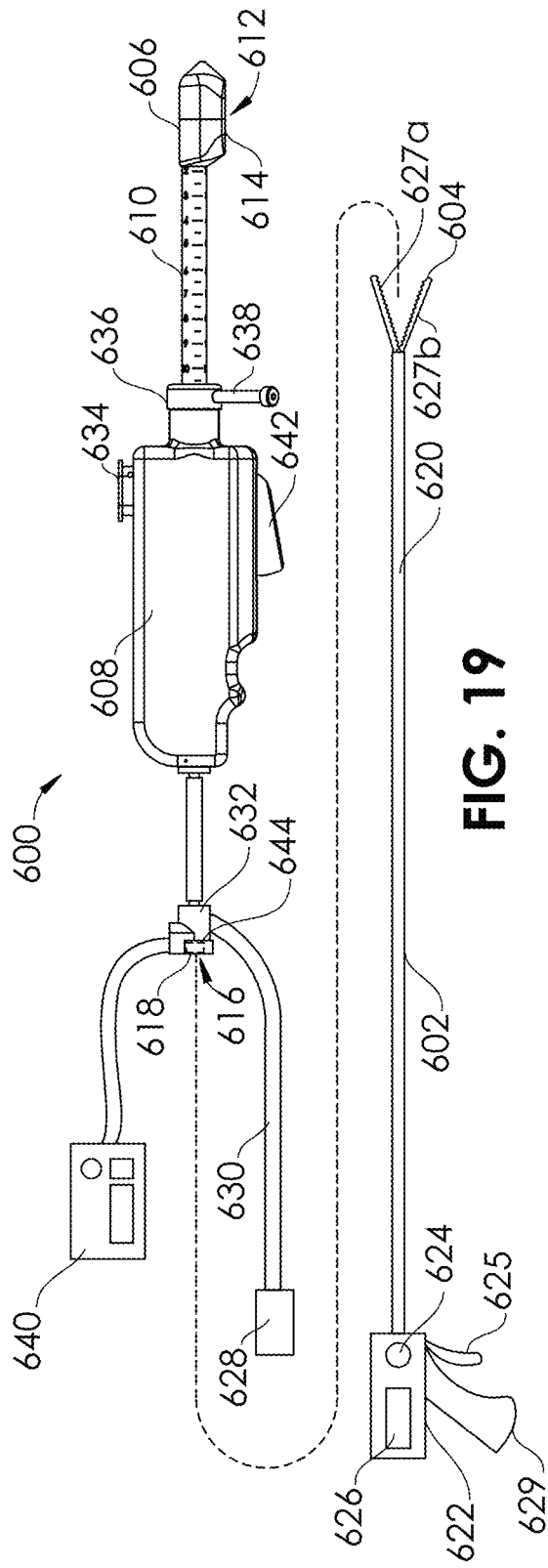
FIG. 19 is an elevation view of a system for closing a blood vessel according to an embodiment of the disclosure.
Figure 20:
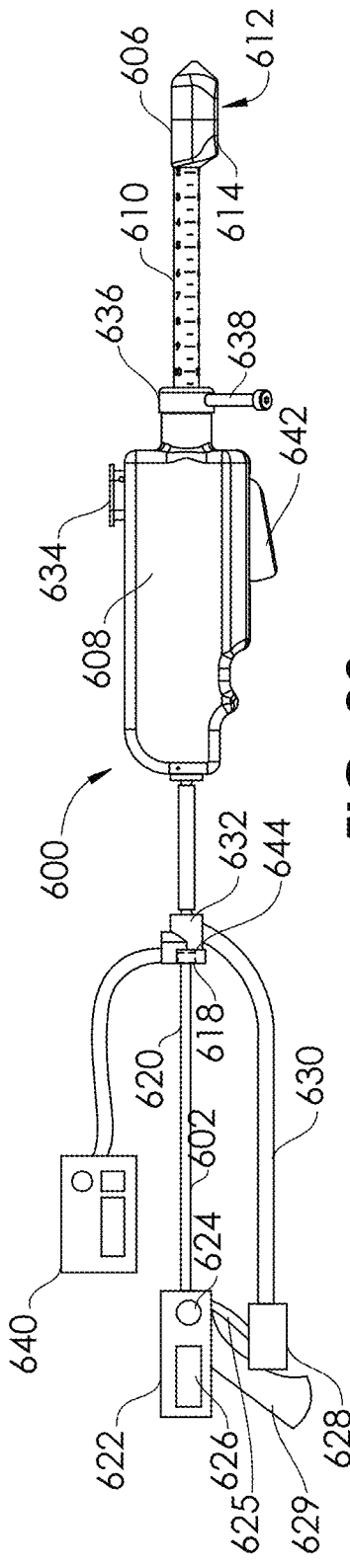
FIG. 20 is an elevation view of the system of FIG. 19 in use.

A system for closure of a blood vessel 600 is illustrated in FIGS. 19-20 according to an embodiment of the disclosure. A housing 608 is coupled to a tubular shaft 610, which is coupled to a distal housing 606. The distal housing 606 includes a cavity 612 having an opening 614 at the side of the distal housing 606. A lumen 616 (e.g., channel) extends between a proximal opening 618 and the opening 614 in the distal housing 606. The lumen 616 is configured for accommodating placement of one or more probes 602, each having a shaft 620 with a vessel closure module 604 at its distal end. In FIG. 19, the vessel closure module 604 comprises a clamp for closing a mass of tissue, including a blood vessel. The probe 602 may be controlled via a control module 622, which includes a switch 624 and/or a handle 629 having a trigger 625, and a display 626. The switch 624 may be configured to automatically cause a pair of jaws 627a, 627b of the clamp (vessel closure module 604) to close. The switch 624 may be operated by the user to apply a current to the jaws 627a, 627b, in order to cauterize the tissue. Alternatively, or in conjunction, the switch 624 may cause the jaws 627a, 627b to automatically close. The user may in some cases cause the clamp to close first, and then, while the clamp is closed, apply the current (cauterize). In other cases, the user may apply the current and then close the clamp while the current is being applied. Alternatively, the switch 624 may be used to detach the clamp from the probe 602, if the clamp is a detachable/implantable clip. As with the other embodiments presented herein, a vacuum source 628 is configured to be coupled to the cavity 612 of the distal housing 606, in this case, via the lumen 616. An extension tube 630 couples the vacuum source 628 to the lumen 616 via a connector 632. A vacuum is applied by a vacuum button 634 which is operable by the hand of a user. The distal housing 606 may be rotated along with the tubular shaft 610 by rotating a distal cap 636 and transverse extension 638. In embodiments that incorporate one or more Doppler sensors, a Doppler console 640 (which may be similar to Doppler console 204) is coupled to the Doppler sensor(s) via the connector 632. A spring-loaded lever 642 may be carried by the housing 608, to aid in the advancement of the probe 602, for example, by the repetitive, longitudinally-directed frictional engagement of the shaft 620. For example, each time the lever 642 is depressed, the shaft 620 is frictionally engaged and the shaft 620 is advanced distally a particular finite longitudinal distance in relation to the housing 608 and tubular shaft 610. The release of the lever 642, because it undoes the frictional engagement with the shaft 620, does not move the shaft 620 longitudinally. The connector 632 includes a seal 644 which may be configured in several different manners. First, the seal 644 may be a permanent seal, such as a duckbill valve or spring-activated valve, so that the proximal opening 618 is closed (sealed) when no probes 602 are within the lumen 616, and so that the proximal opening 618 seals around the diameter of the shaft 620 when the probe 602 is within the lumen. Alternatively, the seal 644 may be configured to seal only when the probe 602 is within the lumen, and may comprise an o-ring, a Touhy-Borst or a spring-loaded valve. An introducer may be used to more easily insert the vessel closure module 604 of the probe 602 into the lumen 616.

FIG. 20 shows the probe 602 inserted into the lumen 616, and with the closure module 604 advanced so that it is within the cavity 612 of the distal housing 606. In use, the user applies a vacuum to the cavity 612 by pressing the vacuum button 634. The target tissue is pulled into the cavity 612 and the vessel closure module 604 is activated. For example, the tissue is clamped, to close the blood vessel within the tissue (e.g., hemorrhoidal artery, etc.). If more than one vessel closure module 604 needs to be applied to the tissue (or to more than one portion of the tissue), then the probe 602 may be removed from the lumen 616, and another probe 602 may be advanced through the lumen 616, with the treatment steps repeated. This may be repeated with any number of different probes 602, including probes of more than one modality (cautery, clip, staple, ligator, etc.). The housing 608/tubular shaft 610/distal housing 606 thus together can, in some cases, maintain a particular position adjacent to target tissue, while a number of different probes 602 can quickly and easily be advanced, applied, and removed in succession, to fully treat the target tissue. The speed of the procedure can thus be increased, because the distal housing 606 does not have to be readvanced or repositioned. Additionally, the sizes of the tubular shaft 610 and distal housing 606 can be reduced, for easier passage through body tracts or cavities, as they only need to accommodate a single probe 602 or vessel closure module 604 at a time, and not fit multiple probes or modules.

Figure 21:
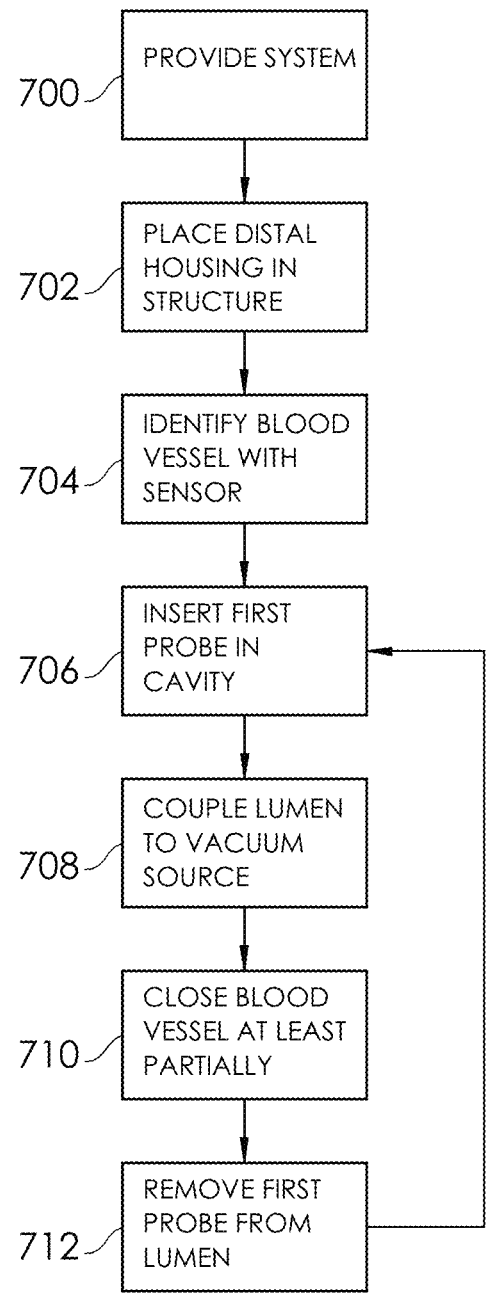
FIG. 21 is a flow chart of a method for closing a blood vessel according to an embodiment of the disclosure.

FIG. 21 illustrates a method for closing a blood vessel. The method may include closing a hemorrhoidal artery in a subject, for example, by placement of a device within a natural lumen or cavity of the subject, adjacent the hemorrhoidal artery. In step 700, a system is provided which is configured for placement adjacent a blood vessel. The system may comprise the system for closure of a blood vessel 400 of FIGS. 15 and 16, or the system for closure of a blood vessel 500 of FIGS. 17 and 18, or the system for closure of a blood vessel 600 of FIGS. 19 and 20, or another system having similar characteristics or parallel indications. In some embodiments, the system may include a housing having a proximal end and a distal end and configured to be held in the hand of a user. The system further includes an elongate body extending from the distal end of the housing and configured for insertion adjacent a blood vessel within a subject. In some embodiments, the elongate body is configured for insertion within a natural lumen or cavity of the subject. In some embodiments, the elongate body is configured for insertion into the anus of the subject. In some embodiments, the elongate body is configured for insertion into the rectum of the subject. The system further includes a distal housing having a proximal end coupled to the distal end of the elongate body, and having a cavity contained therein. The cavity may include an opening on a side of the distal housing. The system further includes a lumen passing through the elongate body and terminating at the cavity of the distal housing. The lumen is configured to couple to a vacuum source and is configured to allow the insertion and removal of a probe having a vessel closure module carried at its distal end. The lumen is configured to maintain a vacuum within the cavity when the probe is within the lumen and the vessel closure module is within the cavity. The system further includes a sensor carried by the distal housing adjacent the cavity and configured for identifying a blood vessel. The sensor may include one or more of: a Doppler sensor, an infra-red sensor, a near infra-red sensor, an optical coherence tomography (OCT) sensor, and may or may not include one or more optical fibers.

In step 702, the distal housing of the system is placed within an internal structure of a subject to be treated. The distal housing of the system may be placed in a natural lumen or cavity, which may or may not include the anus and/or the rectum. In step 704 a blood vessel is identified at least partially by use of the sensor. For example, the sensor is operated while the user moves the distal housing until the sensor detects the blood vessel at a location adjacent the distal housing. The distal housing may be moved by the user by the manipulation of the housing and/or the elongate body. Either may be pushed distally, pulled proximally, or rotated in a generally clockwise manner or a generally counterclockwise manner, or a combination of any of the above. In step 706, a first probe having a first vessel closure module is inserted at least partially inserted into the cavity. This may be done after the blood vessel is identified, but in some cases, the first probe may actually be inserted into the cavity prior to the identification of the blood vessel or even prior to the placing of the distal housing within the internal structure of the subject.

In step 708, the lumen is coupled to a vacuum source, which may include a syringe, a vacuum pump, a vacuum chamber, or other device for applying a vacuum. The coupling of the vacuum source allows a vacuum (negative pressure) to be applied at the cavity, thus allowing tissue of the subject to be pulled into the cavity to facilitate treatment of the tissue. The tissue may for example include the blood vessel which is intended for closure. In step 710, the blood vessel is at least partially closed by operation of the first vessel closure module of the first probe. In some embodiments, the first vessel closure module may comprise a cautery device, and may comprise a wire loop or two opposing jaws (e.g., clamp). The first vessel closure module may at least partially close the blood vessel via cautery. In some embodiments, the first vessel closure module may comprise a ligation tie or other ligator. In some embodiments, the first vessel closure module may comprise a clamp. In some embodiments, the first vessel closure module may comprise a clip. Though the blood vessel may be completely closed by the first vessel closure module, it may also be desired to remove the first vessel closure module and replace it with another (i.e., second) vessel closure module, either a vessel closure module similar to the first vessel closure module, or a vessel closure module having a different structure or modality. In some cases, the second vessel closure module may be carried by the first probe that was used in conjunction with the first vessel closure module. For example, the first vessel closure module may be removed from the first probe and the second vessel closure module may be attached to the first probe. In other cases, a second probe having a second vessel closure module may be used to replace the first probe having the first vessel closure module.

In step 712, the first probe is removed from the lumen. In some cases, for example, cases wherein the treatment of the blood vessel has been completed, the procedure may be ended after step 712. In other cases, further treatment may be desired, and thus step 706 is repeated, but now with a second probe having a second vessel closure module (or the first probe which has had its first vessel closure module replaced or augmented by the second vessel closure module). One or more of the other steps may be repeated with the second probe/vessel closure module combination. A number of different probes and/or vessel closure modules may be inserted (step 706), operated (step 710), and removed (step 712). Up to 5, 10, 20, or more different probes may be used in any procedure. The stability and location maintenance of the housing 408, 508, 608, the tubular shaft 410, 510, 610 and the distal housing 406, 506, 606 allow for rapid removal and replacement of probes 402, 502, 602. The coupling of the vacuum source (step 708) may be maintained throughout, or may continually be applied. A combination of different modalities of vessel closure modules may be used, or different geometries or sizes of vessel closure modules or probes may be used. In some cases, the user may start with a small vessel closure module progress, probe-by-probe to larger and larger vessel closure modules, or start with a low energy vessel closure module and progress to high energy vessel closure modules. On other cases, the user may begin with a large or high energy vessel closure module that performs the majority of the closure procedure, and then replace the vessel closure module with one or more smaller or lower energy vessel closure modules to "touch up" or to finish the procedure. In some cases, multiple probes having the same type of vessel closure module may be used, for example, a new vessel closure module to replace a worn out or exhausted vessel closure module.

The sensor allows correct or desired placement of the distal housing, and the sensor and/or the supporting structure of the housing, elongate body, and distal housing allows this placement to be maintained once it is achieved. Thus, a user does not need to continually insert the distal housing or rotate the distal housing to find the target anatomy. Simple insertion and removal of multiple probes can be quickly and accurately performed, thus allowing for a rapid and efficient procedure. At any time, a slight adjustment to the location of the distal housing may be performed by operating the sensor and determining the desired location of the distal housing in relation to the blood vessel.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

What is claimed is:

1. A system for closing a blood vessel, comprising:
a distal housing configured for insertion into the rectum of a subject, and having a cavity therein, the cavity communicating with an opening on a side of the distal housing;
a lumen communicating with the cavity of the distal housing, the lumen configured to couple to a vacuum source;
a first sensor carried by the distal housing at or adjacent the cavity and configured for identifying a blood vessel;
a vessel closure probe having a longitudinal axis and comprising a distal end operable within the cavity and coupled to a proximal control, the distal end comprising a cauterizer comprising two opposing elongate jaws, the jaws having an open configuration and a closed configuration, wherein in the open configuration at least a distal portion of a first one of the jaws is separated from a distal portion of a second of the jaws and wherein in the closed configuration the distal portions of the jaws meet each other along the longitudinal axis with the jaws co-extending substantially longitudinally, and wherein the jaws are configured to be moved via the proximal control from the open configuration toward the closed configuration over tissue containing the blood vessel; and
an internal seal configured to seal a proximal entrance to the cavity around the vessel closure probe, proximal to the two opposing jaws, to allow a vacuum to be applied by the vacuum source to the cavity with the two opposing jaws inside the cavity.

2. The system of claim 1, wherein the two opposing jaws are bipolar driven.

3. The system of claim 1, wherein the first sensor comprises a Doppler sensor.

4. The system of claim 1, wherein the first sensor comprises an infra-red sensor.

5. The system of claim 1, wherein the first sensor comprises a near infra-red sensor.

6. The system of claim 1, wherein the first sensor comprises an optical coherence tomography sensor.

7. The system of claim 1, wherein the first sensor comprises one or more optical fibers.

8. The system of claim 1, wherein the vessel closure probe is configured to be removed from the cavity.

9. The system of claim 1, further comprising a switch configured to apply current to the two opposing jaws.

10. The system of claim 1, further comprising a proximal handle including a first portion and a second portion movable in relation to the first portion to close the two opposing jaws on the tissue containing the blood vessel within the cavity.

11. The system of claim 1, wherein the distal housing is configured to be rotatable by a user while it is within the rectum of the subject.

12. The system of claim 1, further comprising a transversely extending projection configured for rotating the distal housing within the rectum of the subject.

13. The system of claim 1, wherein the first sensor is carried within the cavity.

14. The system of claim 13, further comprising a second sensor carried by the distal housing at or adjacent the cavity and configured for identifying the blood vessel.

15. The system of claim 14, wherein the first sensor and the second sensor are aimed in different directions.

16. A method for closing a blood vessel comprising:
providing a system for closing a blood vessel comprising:
a distal housing configured for insertion into the rectum of a subject, and having a cavity therein, the cavity communicating with an opening on a side of the distal housing;
a lumen communicating with the cavity of the distal housing, the lumen configured to couple to a vacuum source;
a first sensor carried by the distal housing at or adjacent the cavity and configured for identifying a blood vessel;
a vessel closure probe having a longitudinal axis and comprising a distal end operable within the cavity and coupled to a proximal control, the distal end comprising a cauterizer comprising two opposing elongate jaws, the jaws having an open configuration and a closed configuration, wherein in the open configuration at least a distal portion of a first one of the jaws is separated from a distal portion of a second one of the jaws and wherein in the closed configuration the distal portions of the jaws meet each other along the longitudinal axis with the jaws co-extending substantially longitudinally, and wherein the jaws are configured to be moved via the proximal control from the open configuration toward the closed configuration over tissue containing the blood vessel; and
an internal seal configured to seal a proximal entrance to the cavity around the vessel closure probe, proximal to the two opposing jaws, to allow a vacuum to be applied by the vacuum source to the cavity with the two opposing jaws inside the cavity;
placing the distal housing within an internal structure of a subject;
identifying at least partially with the sensor a blood vessel to be closed;
coupling a vacuum source to the lumen such that a portion of the blood vessel is pulled into the cavity; and
at least partially closing the blood vessel with the vessel closure probe by causing the two opposing jaws to close on tissue containing the blood vessel and causing cauterization to occur.

17. The method of claim 16, wherein at least partially identifying the blood vessel comprises delivering ultrasound signals.

18. The method of claim 16, further comprising rotating the distal housing within the internal structure of the subject.

19. The method of claim 16, wherein the two opposing jaws are bipolar driven, and wherein the cauterization is caused by applying current to the two opposing jaws.

20. The method of claim 16, further comprising removing the vessel closure probe from the cavity.

* * * * *